US006274790B1

(12) United States Patent
Kunst et al.

(10) Patent No.: US 6,274,790 B1
(45) Date of Patent: Aug. 14, 2001

(54) NUCLEIC ACIDS ENCODING A PLANT ENZYME INVOLVED IN VERY LONG CHAIN FATTY ACID SYNTHESIS

(75) Inventors: Ljerka Kunst, North Vancouver; Anthony A. Millar, Vancouver, both of (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 09/058,947

(22) Filed: Apr. 10, 1998

Related U.S. Application Data

(60) Provisional application No. 60/043,831, filed on Apr. 14, 1997.

(51) Int. Cl.[7] .............................. C12N 15/82; A01H 5/00; C07H 21/04
(52) U.S. Cl. .......................... 800/287; 800/281; 800/298; 435/468; 536/24.1
(58) Field of Search ..................................... 800/298, 281, 800/264, 287; 435/69.1, 468, 419, 430, 320.1; 536/23.6

(56) References Cited

U.S. PATENT DOCUMENTS

| | | |
|---|---|---|
| 5,443,974 | 8/1995 | Hitz et al. . |
| 5,455,167 | 10/1995 | Voelker et al. . |
| 5,530,192 | 6/1996 | Murase et al. . |

FOREIGN PATENT DOCUMENTS

| | | |
|---|---|---|
| 4433307A | 3/1996 | (DE) . |
| WO95/15387 | 6/1995 | (WO) . |
| WO96/13582 | 5/1996 | (WO) . |

OTHER PUBLICATIONS

Benfey et al., Science 250:959–966, Nov. 1990.*
Newman et al., "AC T22193," EMBL Database, Jun. 27, 1994.
Newman et al., "AC T76616," EMBL Database, Mar. 25, 1995.
Sohal & Jenkins, "Epidermal–specific gene expression in Brassica and Arabidopsis," Plant Physiology Supplement, vol. 111, No. 2, p. 6, Jun. 2, 1996.
Evenson & Post–Beittenmiller, "Fatty acid–elongation activity in rapidly expanding leek epidermis," Plant Physiology, vol. 109, pp. 707–716, 1995.
Millar & Kunst, "Very–long–chain fatty acid biosynthesis is controlled through the expression and specificity of the condensing enzyme" The Plant Journal 12(1):121–131, 1997.
Newman et al., "Genes Galore: A Summary of Methods for Accessing Results from Large–Scale Partial Sequencing of Anonymous Arabidopsis cDNA Clones" Plant Physiol., 106:1241–1255, 1994.
Katavic et al., "In planta transformation of *Arabidopsis thaliana*" Mol Gen Genet, 245:363–370, 1994.
Lemieux, "Molecular genetics of epicuticular wax biosynthesis" Trends in Plant Science, 1(9):312–318, 1996.
Kunst et al., "Fatty acid elongation in developing seeds of *Arabidopsis thaliana*" Plant Physiol. Biochem., 30:(4) 425–434, 1992.
Lassner et al., "A Jojoba β–Ketoacyl–CoA Synthase cDNA Complements the Canola Fatty Acid Elongation Mutation in Transgenic Plants" The Plant Cell, 8:281–292, 1996.
James et al., "Directed Tagging of the Arabidopsis Fatty Acid Elongation 1 (FAE1) Gene with the Maize Transposon Activator," The Plant Cell, 7:309–319, 1995.
James & Dooner, "Isolation of EMS–induced mutants in Arabidopsis altered in seed fatty acid composition" Theor Appl Genet, 80:241–245, 1990.
Lemieux et al., "Mutants of Arabidopsis with alterations in seed lipid fatty acid composition" Theor Appl Genet, 80:234–240, 1990.

\* cited by examiner

*Primary Examiner*—Elizabeth F. McElwain
(74) *Attorney, Agent, or Firm*—Klarquist Sparkman Campbell Leigh & Whinston, LLP

(57) ABSTRACT

Nucleic acid molecules encoding an enzyme involved in very long chain fatty acid (VLCFA) elongation in plants are disclosed. The invention includes a cDNA, genomic clone and encoded protein, as well as plants having modified VLCFA composition, such as modified epicuticular waxes, and methods of making such plants.

12 Claims, 1 Drawing Sheet

Arabidopsis Wax Biosynthesis

Figure 1:
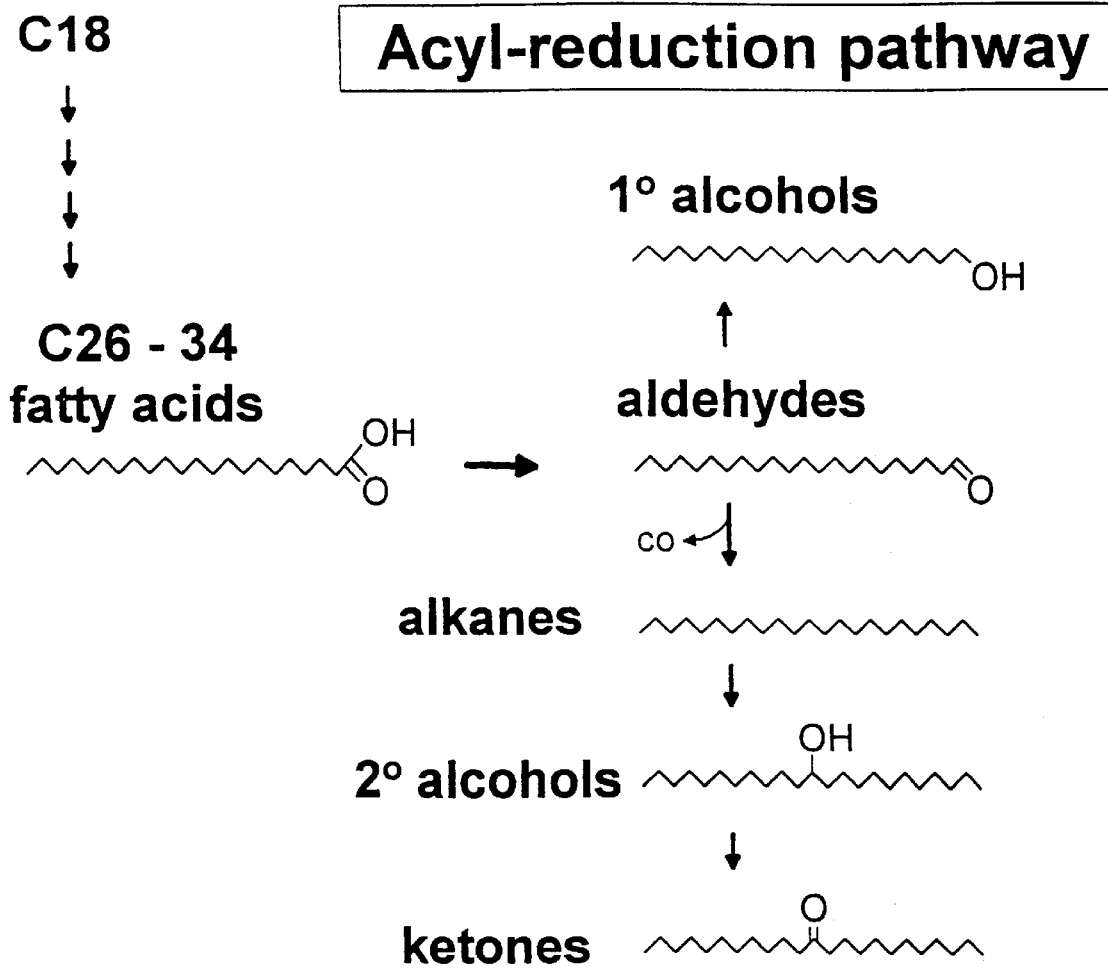

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
        (A) LENGTH: 3722
        (B) TYPE: nucleic acid
        (C) STRANDEDNESS: double
        (D) TOPOLOGY: linear (xi) SEQUENCE DESCRIPTION: SEQ ID NO: 1:

```
TAGTGCTTTA TATATGTTTG ATACTTCTGT TTGGCAATAT CAATCATAGT          50

AGAAAAGATA TGGACTTCAT TTGAGGTTTT TGGTGGATTG TGTCTATATG         100

TGAAATCATG GGATCTCAAG ATTTGTCTGC ATTCAGTTTC CAAGTCAAAC         150

ATCGTAACTA CTGTTTGATT TTCCCTCATG CTTGCAGTTT TCATGGATAT         200

CTCAAGATTT GTCTTCTTGC ACTTTCCAAG TCAAACATAA AGTAACTACT         250

GATTGATATT CCCTCGTGTA TTACCCTCTT TCAAATGACA CAATTGGGCC         300

CAAGTAGAGG AATTTCATAG TGAATTCAAA AGATTAACTG TATTCCACCG         350

TCGTATTTTG ATAACATTTA GTTATTCCTT TTCTTTTTTT TCTTCTGCAA         400

CAGTTTTTTT TTAATACATT TAGTGTTGGT TTGGTTCAAT GAAATATTAT         450

ATGTTACTTC TTTTTTTGGA AATAAATTAT TCATTCTTTC TACTATAAAA         500

GGAATTGTTC ATGCTTTTTT GATACAATAG TATACCATTT CAAAAGATAC         550

CATAGACCAG TTATTACATG AATCGCCAAA ACAACACTAA AATCAGAAAA         600

TCAGTATATT TTGGTATAGT CTCCAACATA CAATCATAAA ACCTCTGTGA         650

AATTTAAAAT CTATATTTGA CATTTCAAAG TTTAACAACA TAGTTCTAAA         700

TAATTACCTA AATTTTAAGT CAAATGTGAA TTATATTTTA CTCTTCGATA         750

TCGGTTGTTG ACGATTAACC ATGCAAAAAA GAAACATTAA TTGCGAATGT         800

AAATAACAAA ACATGTAACT CTTGTAGATA TACATGTATC GACATTTAAA         850

CCCGAATATA TATGTATACC TATAATTTCT CTGATTTTCA CGCTACCTGC         900

CACGTACATG GGTGATAGGT CCAAACTCAC AAGTAAAAGT TTACGTACAG         950

TGAATTCGTC TTTTTGGGTA TAAACGTACA TTTAATTTAC ACGTAAGAAA        1000

GGATTACCAA TTCTTTCATT TATGGTACCA GACAGAGTTA AGGCAAACAA        1050

GAGAAACATA TAGAGTTTTG ATATGTTTTC TTGGATAAAT ATTAAATTGA        1100

TGCAATATTT AGGGATGGAC ACAAGGTAAT ATATGCCTTT TAAGGTATAT        1150

GTGCTATATG AATCGTTTCG CATGGGTACT AAAATTATTT GTCCTTACTT        1200
```

```
TATATAAACA AATTCCAACA AAATCAAGTT TTTGCTAAAA CTAGTTTATT      1250

TGCGGGTTAT TTAATTACCT ATCATATTAC TTGTAATATC ATTCGTATGT      1300

TAACGGGTAA ACCAAACCAA ACCGGATATT GAACTATTAA AAATCTTGTA      1350

AATTTGACAC AAACTAATGA ATATCTAAAT TATGTTACTG CTATGATAAC      1400

GACCATTTTT GTTTTTGAGA ACCATAATAT AAATTACAGG TACGTGACAA      1450

GTACTAAGTA TTTATATCCA CCTTTAGTCA CAGTACCAAT ATTGCGCCTA      1500

CCGGGCAACG TGAACGTGAT CATCAAATCA AAGTAGTTAC CAAACGCTTT      1550

GATCTCGATA AAACTAAAAG CTGACACGTC TTGCTGTTTC TTAATTTATT      1600

TCTCTTACAA CGACAATTTT GAGAAATATG AAATTTTTAT ATCGAAAGGG      1650

AACAGTCCTT ATCATTTGCT CCCATCACTT GCTTTTGTCT AGTTACAACT      1700

GGAAATCGAA GAGAAGTATT ACAAAAACAT TTTTCTCGTC ATTTATAAAA      1750

AAATGACAAA AAATTAAATA GAGAGCAAAG CAAGAGCGTT GGGTGACGTT      1800

GGTCTCTTCA TTAACTCCTC TCATCTACCC CTTCCTCTGT TCGCCTTTAT      1850

ATCCTTCACC TTCCCTCTCT CATCTTCATT AACTCATCTT CAAAAATACC      1900

CTAATCACAT TTTGTAACAA TAATACAATT ATACATTAAA ACTCTCCGAC      1950
```

| | | |
|---|---|---|
| G ATG CCT CAG GCA CCG ATG CCA GAG TTC TCT AGC TCG GTG<br>  Met Pro Gln Ala Pro Met Pro Glu Phe Ser Ser Ser Val<br>  1               5                   10 | | 1990 |
| AAG CTC AAG TAC GTG AAA CTT GGT TAC CAA TAT TTG GTT AAC<br>Lys Leu Lys Tyr Val Lys Leu Gly Tyr Gln Tyr Leu Val Asn<br>        15                  20                  25 | | 2032 |
| CAT TTC TTG AGT TTT CTT TTG ATC CCG ATC ATG GCT ATT GTC<br>His Phe Leu Ser Phe Leu Leu Ile Pro Ile Met Ala Ile Val<br>            30                  35                  40 | | 2074 |
| GCC GTT GAG CTT CTT CGG ATG GGT CCT GAA GAG ATC CTT AAT<br>Ala Val Glu Leu Leu Arg Met Gly Pro Glu Glu Ile Leu Asn<br>                45                  50                  55 | | 2116 |
| GTT TGG AAT TCA CTC CAG TTT GAC CTA GTT CAG GTT CTA TGT<br>Val Trp Asn Ser Leu Gln Phe Asp Leu Val Gln Val Leu Cys<br>                    60                  65 | | 2158 |
| TCT TCC TTC TTT GTC ATC TTC ATC TCC ACT GTT TAC TTC ATG<br>Ser Ser Phe Phe Val Ile Phe Ile Ser Thr Val Tyr Phe Met<br>70                  75                  80 | | 2200 |
| TCC AAG CCA CGC ACC ATC TAC CTC GTT GAC TAT TCT TGT TAC<br>Ser Lys Pro Arg Thr Ile Tyr Leu Val Asp Tyr Ser Cys Tyr<br>        85                  90                  95 | | 2242 |
| AAG CCA CCT GTC ACG TGT CGT GTC CCC TTC GCA ACT TTC ATG<br>Lys Pro Pro Val Thr Cys Arg Val Pro Phe Ala Thr Phe Met<br>            100                 105                 110 | | 2284 |
| GAA CAC TCT CGT TTG ATC CTC AAG GAC AAG CCT AAG AGC GTC<br>Glu His Ser Arg Leu Ile Leu Lys Asp Lys Pro Lys Ser Val<br>                115                 120                 125 | | 2326 |
| GAG TTC CAA ATG AGA ATC CTT GAA CGT TCT GGC CTC GGT GAG<br>Glu Phe Gln Met Arg Ile Leu Glu Arg Ser Gly Leu Gly Glu<br>                    130                 135 | | 2368 |
| GAG ACT TGT CTC CCT CCG GCT ATT CAT TAT ATT CCT CCC ACA<br>Glu Thr Cys Leu Pro Pro Ala Ile His Tyr Ile Pro Pro Thr<br>140                 145                 150 | | 2410 |
| CCA ACC ATG GAC GCG GCT AGA AGC GAG GCT CAG ATG GTT ATC<br>Pro Thr Met Asp Ala Ala Arg Ser Glu Ala Gln Met Val Ile<br>        155                 160                 165 | | 2452 |

```
TTC GAG GCC ATG GAC GAT CTT TTC AAG AAA ACC GGT CTT AAA           2494
Phe Glu Ala Met Asp Asp Leu Phe Lys Lys Thr Gly Leu Lys
            170                 175                 180

CCT AAA GAC GTC GAC ATC CTT ATC GTC AAC TGC TCT CTT TTC           2536
Pro Lys Asp Val Asp Ile Leu Ile Val Asn Cys Ser Leu Phe
            185                 190                 195

TCT CCC ACA CCA TCG CTC TCA GCT ATG GTC ATC AAC AAA TAT           2578
Ser Pro Thr Pro Ser Leu Ser Ala Met Val Ile Asn Lys Tyr
                200                 205

AAG CTT AGG AGT AAT ATC AAG AGC TTC AAT CTT TCG GGG ATG           2620
Lys Leu Arg Ser Asn Ile Lys Ser Phe Asn Leu Ser Gly Met
210                 215                 220

GGC TGC AGC GCG GGC CTG ATC TCA GTT GAT CTA GCC CGC GAC           2662
Gly Cys Ser Ala Gly Leu Ile Ser Val Asp Leu Ala Arg Asp
        225                 230                 235

TTG CTC CAA GTT CAT CCC AAT TCA AAT GCA ATC ATC GTC AGC           2704
Leu Leu Gln Val His Pro Asn Ser Asn Ala Ile Ile Val Ser
            240                 245                 250

ACG GAG ATC ATA ACG CCT AAT TAC TAT CAA GGC AAC GAG AGA           2746
Thr Glu Ile Ile Thr Pro Asn Tyr Tyr Gln Gly Asn Glu Arg
                255                 260                 265

GCC ATG TTG TTA CCC AAT TGT CTC TTC CGC ATG GGT GCG GCA           2788
Ala Met Leu Leu Pro Asn Cys Leu Phe Arg Met Gly Ala Ala
                    270                 275

GCC ATA CAC ATG TCA AAC CGC CGG TCT GAC CGG TGG CGA GCC           2830
Ala Ile His Met Ser Asn Arg Arg Ser Asp Arg Trp Arg Ala
280                 285                 290

AAA TAC AAG CTT TCC CAC CTC GTC CGG ACA CAC CGT GGC GCT           2872
Lys Tyr Lys Leu Ser His Leu Val Arg Thr His Arg Gly Ala
        295                 300                 305

GAC GAC AAG TCT TTC TAC TGT GTC TAC GAA CAG GAA GAC AAA           2914
Asp Asp Lys Ser Phe Tyr Cys Val Tyr Glu Gln Glu Asp Lys
            310                 315                 320

GAA GGA CAC GTT GGC ATC AAC TTG TCC AAA GAT CTC ATG GCC           2956
Glu Gly His Val Gly Ile Asn Leu Ser Lys Asp Leu Met Ala
                325                 330                 335

ATC GCC GGT GAA GCC CTC AAG GCA AAC ATC ACC ACA ATA GGT           2998
Ile Ala Gly Glu Ala Leu Lys Ala Asn Ile Thr Thr Ile Gly
                    340                 345

CCT TTG GTC CTA CCG GCG TCA GAA CAA CTT CTC TTC CTC ACG           3040
Pro Leu Val Leu Pro Ala Ser Glu Gln Leu Leu Phe Leu Thr
350                 355                 360

TCC CTA ATC GGA CGT AAA ATC TTC AAC CCG AAA TGG AAA CCA           3082
Ser Leu Ile Gly Arg Lys Ile Phe Asn Pro Lys Trp Lys Pro
        365                 370                 375

TAC ATA CCG GAT TTC AAG CTG GCC TTC GAA CAC TTT TGC ATT           3124
Tyr Ile Pro Asp Phe Lys Leu Ala Phe Glu His Phe Cys Ile
            380                 385                 390

CAC GCA GGA GGC AGA GCG GTG ATC GAC GAG CTC CAA AAG AAT           3166
His Ala Gly Gly Arg Ala Val Ile Asp Glu Leu Gln Lys Asn
                395                 400                 405

CTA CAA CTA TCA GGA GAA CAC GTT GAG GCC TCA AGA ATG ACA           3208
Leu Gln Leu Ser Gly Glu His Val Glu Ala Ser Arg Met Thr
                    410                 415

CTA CAT CGT TTT GGT AAC ACG TCA TCT TCA TCG TTA TGG TAC           3250
Leu His Arg Phe Gly Asn Thr Ser Ser Ser Ser Leu Trp Tyr
420                 425                 430

GAG CTT AGC TAC ATC GAG TCT AAA GGG AGA ATG AGG AGA GGC           3292
Glu Leu Ser Tyr Ile Glu Ser Lys Gly Arg Met Arg Arg Gly
        435                 440                 445
```

```
GAT CGC GTT TGG CAA ATC GCG TTT GGG AGT GGT TTC AAG TGT                3334
Asp Arg Val Trp Gln Ile Ala Phe Gly Ser Gly Phe Lys Cys
        450                 455                 460

AAC TCT GCC GTG TGG AAA TGT AAC CGT ACG ATT AAG ACA CCT                3376
Asn Ser Ala Val Trp Lys Cys Asn Arg Thr Ile Lys Thr Pro
            465                 470                 475

AAG GAC GGA CCA TGG TCC GAT TGT ATC GAC CGT TAC CCT GTC                3418
Lys Asp Gly Pro Trp Ser Asp Cys Ile Asp Arg Tyr Pro Val
                480                 485

TTT ATT CCC GAA GTT GTC AAA CTC TAA ACTGA                              3450
Phe Ile Pro Glu Val Val Lys Leu
490                 495

AAACGTCTTT GAACGGTTTA GTAACGGTTT GATTTTGTGT TACGGTTTAG                 3500

GTTTATTTGG TCTCGGGATT TGGTTTAAAG GGGATTGAGA AATGGGAAGT                 3550

TAGAGAGAAG AAAAAGCAAA GCATAAATGT TTGTATTTAA TTGCTCTGCA                 3600

TATACTTAAA TCTCTGCTTT TCATTTGGGG TATTTTTTAG TTTCTCGTGC                 3650

TGTAATTAAT AACTTGTGGT GTACTCAAAT AAGAATATTT CTCTCTGTTT                 3700

AAAAAAAAAA AAAAAAAAAA AA                                               3722

(2) INFORMATION FOR SEQ ID NO:2:

(i) SEQUENCE CHARACTERISTICS:
        (A) LENGTH: 1807
        (B) TYPE: nucleic acid
        (C) STRANDEDNESS: double
        (D) TOPOLOGY: linear (xi) SEQUENCE DESCRIPTION: SEQ ID NO: 2:

AAATACC                                                                   7

CTAATCACAT TTTGTAACAA TAATACAATT ATACATTAAA ACTCTCCGAC                   57

G ATG CCT CAG GCA CCG ATG CCA GAG TTC TCT AGC TCG GTG                   97
  Met Pro Gln Ala Pro Met Pro Glu Phe Ser Ser Ser Val
  1               5                   10

AAG CTC AAG TAC GTG AAA CTT GGT TAC CAA TAT TTG GTT AAC                 139
Lys Leu Lys Tyr Val Lys Leu Gly Tyr Gln Tyr Leu Val Asn
        15                  20                  25

CAT TTC TTG AGT TTT CTT TTG ATC CCG ATC ATG GCT ATT GTC                 181
His Phe Leu Ser Phe Leu Leu Ile Pro Ile Met Ala Ile Val
            30                  35                  40

GCC GTT GAG CTT CTT CGG ATG GGT CCT GAA GAG ATC CTT AAT                 223
Ala Val Glu Leu Leu Arg Met Gly Pro Glu Glu Ile Leu Asn
                45                  50                  55

GTT TGG AAT TCA CTC CAG TTT GAC CTA GTT CAG GTT CTA TGT                 265
Val Trp Asn Ser Leu Gln Phe Asp Leu Val Gln Val Leu Cys
                    60                  65

TCT TCC TTC TTT GTC ATC TTC ATC TCC ACT GTT TAC TTC ATG                 307
Ser Ser Phe Phe Val Ile Phe Ile Ser Thr Val Tyr Phe Met
70                  75                  80

TCC AAG CCA CGC ACC ATC TAC CTC GTT GAC TAT TCT TGT TAC                 349
Ser Lys Pro Arg Thr Ile Tyr Leu Val Asp Tyr Ser Cys Tyr
        85                  90                  95

AAG CCA CCT GTC ACG TGT CGT GTC CCC TTC GCA ACT TTC ATG                 391
Lys Pro Pro Val Thr Cys Arg Val Pro Phe Ala Thr Phe Met
            100                 105                 110

GAA CAC TCT CGT TTG ATC CTC AAG GAC AAG CCT AAG AGC GTC                 433
Glu His Ser Arg Leu Ile Leu Lys Asp Lys Pro Lys Ser Val
                115                 120                 125
```

```
GAG TTC CAA ATG AGA ATC CTT GAA CGT TCT GGC CTC GGT GAG         475
Glu Phe Gln Met Arg Ile Leu Glu Arg Ser Gly Leu Gly Glu
                130                 135

GAG ACT TGT CTC CCT CCG GCT ATT CAT TAT ATT CCT CCC ACA         517
Glu Thr Cys Leu Pro Pro Ala Ile His Tyr Ile Pro Pro Thr
140                 145                 150

CCA ACC ATG GAC GCG GCT AGA AGC GAG GCT CAG ATG GTT ATC         559
Pro Thr Met Asp Ala Ala Arg Ser Glu Ala Gln Met Val Ile
        155                 160                 165

TTC GAG GCC ATG GAC GAT CTT TTC AAG AAA ACC GGT CTT AAA         601
Phe Glu Ala Met Asp Asp Leu Phe Lys Lys Thr Gly Leu Lys
            170                 175                 180

CCT AAA GAC GTC GAC ATC CTT ATC GTC AAC TGC TCT CTT TTC         643
Pro Lys Asp Val Asp Ile Leu Ile Val Asn Cys Ser Leu Phe
                185                 190                 195

TCT CCC ACA CCA TCG CTC TCA GCT ATG GTC ATC AAC AAA TAT         685
Ser Pro Thr Pro Ser Leu Ser Ala Met Val Ile Asn Lys Tyr
                    200                 205

AAG CTT AGG AGT AAT ATC AAG AGC TTC AAT CTT TCG GGG ATG         727
Lys Leu Arg Ser Asn Ile Lys Ser Phe Asn Leu Ser Gly Met
210                 215                 220

GGC TGC AGC GCG GGC CTG ATC TCA GTT GAT CTA GCC CGC GAC         769
Gly Cys Ser Ala Gly Leu Ile Ser Val Asp Leu Ala Arg Asp
        225                 230                 235

TTG CTC CAA GTT CAT CCC AAT TCA AAT GCA ATC ATC GTC AGC         811
Leu Leu Gln Val His Pro Asn Ser Asn Ala Ile Ile Val Ser
            240                 245                 250

ACG GAG ATC ATA ACG CCT AAT TAC TAT CAA GGC AAC GAG AGA         853
Thr Glu Ile Ile Thr Pro Asn Tyr Tyr Gln Gly Asn Glu Arg
                255                 260                 265

GCC ATG TTG TTA CCC AAT TGT CTC TTC CGC ATG GGT GCG GCA         895
Ala Met Leu Leu Pro Asn Cys Leu Phe Arg Met Gly Ala Ala
                    270                 275

GCC ATA CAC ATG TCA AAC CGC CGG TCT GAC CGG TGG CGA GCC         937
Ala Ile His Met Ser Asn Arg Arg Ser Asp Arg Trp Arg Ala
280                 285                 290

AAA TAC AAG CTT TCC CAC CTC GTC CGG ACA CAC CGT GGC GCT         979
Lys Tyr Lys Leu Ser His Leu Val Arg Thr His Arg Gly Ala
        295                 300                 305

GAC GAC AAG TCT TTC TAC TGT GTC TAC GAA CAG GAA GAC AAA        1021
Asp Asp Lys Ser Phe Tyr Cys Val Tyr Glu Gln Glu Asp Lys
            310                 315                 320

GAA GGA CAC GTT GGC ATC AAC TTG TCC AAA GAT CTC ATG GCC        1063
Glu Gly His Val Gly Ile Asn Leu Ser Lys Asp Leu Met Ala
                325                 330                 335

ATC GCC GGT GAA GCC CTC AAG GCA AAC ATC ACC ACA ATA GGT        1105
Ile Ala Gly Glu Ala Leu Lys Ala Asn Ile Thr Thr Ile Gly
                    340                 345

CCT TTG GTC CTA CCG GCG TCA GAA CAA CTT CTC TTC CTC ACG        1147
Pro Leu Val Leu Pro Ala Ser Glu Gln Leu Leu Phe Leu Thr
350                 355                 360

TCC CTA ATC GGA CGT AAA ATC TTC AAC CCG AAA TGG AAA CCA        1189
Ser Leu Ile Gly Arg Lys Ile Phe Asn Pro Lys Trp Lys Pro
        365                 370                 375

TAC ATA CCG GAT TTC AAG CTG GCC TTC GAA CAC TTT TGC ATT        1231
Tyr Ile Pro Asp Phe Lys Leu Ala Phe Glu His Phe Cys Ile
            380                 385                 390

CAC GCA GGA GGC AGA GCG GTG ATC GAC GAG CTC CAA AAG AAT        1273
His Ala Gly Gly Arg Ala Val Ile Asp Glu Leu Gln Lys Asn
```

-continued

|  |  |  | 395 |  |  |  | 400 |  |  |  | 405 |  |  |
|---|---|---|---|---|---|---|---|---|---|---|---|---|---|
| CTA | CAA | CTA | TCA | GGA | GAA | CAC | GTT | GAG | GCC | TCA | AGA | ATG | ACA | 1315 |
| Leu | Gln | Leu | Ser | Gly | Glu | His | Val | Glu | Ala | Ser | Arg | Met | Thr |
|  |  |  | 410 |  |  |  | 415 |  |  |  |  |  |  |

```
CTA CAT CGT TTT GGT AAC ACG TCA TCT TCA TCG TTA TGG TAC      1357
Leu His Arg Phe Gly Asn Thr Ser Ser Ser Ser Leu Trp Tyr
420             425             430

GAG CTT AGC TAC ATC GAG TCT AAA GGG AGA ATG AGG AGA GGC      1399
Glu Leu Ser Tyr Ile Glu Ser Lys Gly Arg Met Arg Arg Gly
435             440             445

GAT CGC GTT TGG CAA ATC GCG TTT GGG AGT GGT TTC AAG TGT      1441
Asp Arg Val Trp Gln Ile Ala Phe Gly Ser Gly Phe Lys Cys
        450             455             460

AAC TCT GCC GTG TGG AAA TGT AAC CGT ACG ATT AAG ACA CCT      1483
Asn Ser Ala Val Trp Lys Cys Asn Arg Thr Ile Lys Thr Pro
            465             470             475

AAG GAC GGA CCA TGG TCC GAT TGT ATC GAC CGT TAC CCT GTC      1525
Lys Asp Gly Pro Trp Ser Asp Cys Ile Asp Arg Tyr Pro Val
                480             485

TTT ATT CCC GAA GTT GTC AAA CTC TAA ACTGA                    1557
Phe Ile Pro Glu Val Val Lys Leu

AAACGTCTTT GAACGGTTTA GTAACGGTTT GATTTTGTGT TACGGTTTAG       1607

GTTTATTTGG TCTCGGGATT TGGTTTAAAG GGATTGAGA AATGGGAAGT        1657

TAGAGAGAAG AAAAAGCAAA GCATAAATGT TTGTATTTAA TTGCTCTGCA       1707

TATACTTAAA TCTCTGCTTT TCATTTGGGG TATTTTTTAG TTTCTCGTGC       1757

TGTAATTAAT AACTTGTGGT GTACTCAAAT AAGAATATTT CTCTCTGTTT       1807
```

(2) INFORMATION FOR SEQ ID NO: 3:

(i) SEQUENCE CHARACTERISTICS:
      (A) LENGTH: 1491
      (B) TYPE: nucleic acid
      (C) STRANDEDNESS: double
      (D) TOPOLOGY: linear (xi) SEQUENCE DESCRIPTION: SEQ ID NO: 3:

```
ATG CCT CAG GCA CCG ATG CCA GAG TTC TCT AGC TCG GTG          39
Met Pro Gln Ala Pro Met Pro Glu Phe Ser Ser Ser Val
1               5               10

AAG CTC AAG TAC GTG AAA CTT GGT TAC CAA TAT TTG GTT AAC      81
Lys Leu Lys Tyr Val Lys Leu Gly Tyr Gln Tyr Leu Val Asn
15              20              25

CAT TTC TTG AGT TTT CTT TTG ATC CCG ATC ATG GCT ATT GTC      123
His Phe Leu Ser Phe Leu Leu Ile Pro Ile Met Ala Ile Val
        30              35              40

GCC GTT GAG CTT CTT CGG ATG GGT CCT GAA GAG ATC CTT AAT      165
Ala Val Glu Leu Leu Arg Met Gly Pro Glu Glu Ile Leu Asn
            45              50              55

GTT TGG AAT TCA CTC CAG TTT GAC CTA GTT CAG GTT CTA TGT      207
Val Trp Asn Ser Leu Gln Phe Asp Leu Val Gln Val Leu Cys
                60              65

TCT TCC TTC TTT GTC ATC TTC ATC TCC ACT GTT TAC TTC ATG      249
Ser Ser Phe Phe Val Ile Phe Ile Ser Thr Val Tyr Phe Met
70              75              80

TCC AAG CCA CGC ACC ATC TAC CTC GTT GAC TAT TCT TGT TAC      291
Ser Lys Pro Arg Thr Ile Tyr Leu Val Asp Tyr Ser Cys Tyr
        85              90              95

AAG CCA CCT GTC ACG TGT CGT GTC CCC TTC GCA ACT TTC ATG      333
```

```
Lys Pro Pro Val Thr Cys Arg Val Pro Phe Ala Thr Phe Met
        100                 105                 110

GAA CAC TCT CGT TTG ATC CTC AAG GAC AAG CCT AAG AGC GTC           375
Glu His Ser Arg Leu Ile Leu Lys Asp Lys Pro Lys Ser Val
            115                 120                 125

GAG TTC CAA ATG AGA ATC CTT GAA CGT TCT GGC CTC GGT GAG           417
Glu Phe Gln Met Arg Ile Leu Glu Arg Ser Gly Leu Gly Glu
                130                 135

GAG ACT TGT CTC CCT CCG GCT ATT CAT TAT ATT CCT CCC ACA           459
Glu Thr Cys Leu Pro Pro Ala Ile His Tyr Ile Pro Pro Thr
140                 145                 150

CCA ACC ATG GAC GCG GCT AGA AGC GAG GCT CAG ATG GTT ATC           501
Pro Thr Met Asp Ala Ala Arg Ser Glu Ala Gln Met Val Ile
        155                 160                 165

TTC GAG GCC ATG GAC GAT CTT TTC AAG AAA ACC GGT CTT AAA           543
Phe Glu Ala Met Asp Asp Leu Phe Lys Lys Thr Gly Leu Lys
            170                 175                 180

CCT AAA GAC GTC GAC ATC CTT ATC GTC AAC TGC TCT CTT TTC           585
Pro Lys Asp Val Asp Ile Leu Ile Val Asn Cys Ser Leu Phe
                185                 190                 195

TCT CCC ACA CCA TCG CTC TCA GCT ATG GTC ATC AAC AAA TAT           627
Ser Pro Thr Pro Ser Leu Ser Ala Met Val Ile Asn Lys Tyr
                    200                 205

AAG CTT AGG AGT AAT ATC AAG AGC TTC AAT CTT TCG GGG ATG           669
Lys Leu Arg Ser Asn Ile Lys Ser Phe Asn Leu Ser Gly Met
210                 215                 220

GGC TGC AGC GCG GGC CTG ATC TCA GTT GAT CTA GCC CGC GAC           711
Gly Cys Ser Ala Gly Leu Ile Ser Val Asp Leu Ala Arg Asp
        225                 230                 235

TTG CTC CAA GTT CAT CCC AAT TCA AAT GCA ATC ATC GTC AGC           753
Leu Leu Gln Val His Pro Asn Ser Asn Ala Ile Ile Val Ser
            240                 245                 250

ACG GAG ATC ATA ACG CCT AAT TAC TAT CAA GGC AAC GAG AGA           795
Thr Glu Ile Ile Thr Pro Asn Tyr Tyr Gln Gly Asn Glu Arg
                255                 260                 265

GCC ATG TTG TTA CCC AAT TGT CTC TTC CGC ATG GGT GCG GCA           837
Ala Met Leu Leu Pro Asn Cys Leu Phe Arg Met Gly Ala Ala
                    270                 275

GCC ATA CAC ATG TCA AAC CGC CGG TCT GAC CGG TGG CGA GCC           879
Ala Ile His Met Ser Asn Arg Arg Ser Asp Arg Trp Arg Ala
280                 285                 290

AAA TAC AAG CTT TCC CAC CTC GTC CGG ACA CAC CGT GGC GCT           921
Lys Tyr Lys Leu Ser His Leu Val Arg Thr His Arg Gly Ala
        295                 300                 305

GAC GAC AAG TCT TTC TAC TGT GTC TAC GAA CAG GAA GAC AAA           963
Asp Asp Lys Ser Phe Tyr Cys Val Tyr Glu Gln Glu Asp Lys
            310                 315                 320

GAA GGA CAC GTT GGC ATC AAC TTG TCC AAA GAT CTC ATG GCC          1005
Glu Gly His Val Gly Ile Asn Leu Ser Lys Asp Leu Met Ala
                325                 330                 335

ATC GCC GGT GAA GCC CTC AAG GCA AAC ATC ACC ACA ATA GGT          1047
Ile Ala Gly Glu Ala Leu Lys Ala Asn Ile Thr Thr Ile Gly
                    340                 345

CCT TTG GTC CTA CCG GCG TCA GAA CAA CTT CTC TTC CTC ACG          1089
Pro Leu Val Leu Pro Ala Ser Glu Gln Leu Leu Phe Leu Thr
350                 355                 360

TCC CTA ATC GGA CGT AAA ATC TTC AAC CCG AAA TGG AAA CCA          1131
Ser Leu Ile Gly Arg Lys Ile Phe Asn Pro Lys Trp Lys Pro
        365                 370                 375
```

```
TAC ATA CCG GAT TTC AAG CTG GCC TTC GAA CAC TTT TGC ATT        1173
Tyr Ile Pro Asp Phe Lys Leu Ala Phe Glu His Phe Cys Ile
        380                 385                 390

CAC GCA GGA GGC AGA GCG GTG ATC GAC GAG CTC CAA AAG AAT        1215
His Ala Gly Gly Arg Ala Val Ile Asp Glu Leu Gln Lys Asn
            395                 400                 405

CTA CAA CTA TCA GGA GAA CAC GTT GAG GCC TCA AGA ATG ACA        1257
Leu Gln Leu Ser Gly Glu His Val Glu Ala Ser Arg Met Thr
                410                 415

CTA CAT CGT TTT GGT AAC ACG TCA TCT TCA TCG TTA TGG TAC        1299
Leu His Arg Phe Gly Asn Thr Ser Ser Ser Ser Leu Trp Tyr
420                 425                 430

GAG CTT AGC TAC ATC GAG TCT AAA GGG AGA ATG AGG AGA GGC        1341
Glu Leu Ser Tyr Ile Glu Ser Lys Gly Arg Met Arg Arg Gly
        435                 440                 445

GAT CGC GTT TGG CAA ATC GCG TTT GGG AGT GGT TTC AAG TGT        1383
Asp Arg Val Trp Gln Ile Ala Phe Gly Ser Gly Phe Lys Cys
            450                 455                 460

AAC TCT GCC GTG TGG AAA TGT AAC CGT ACG ATT AAG ACA CCT        1425
Asn Ser Ala Val Trp Lys Cys Asn Arg Thr Ile Lys Thr Pro
                465                 470                 475

AAG GAC GGA CCA TGG TCC GAT TGT ATC GAC CGT TAC CCT GTC        1467
Lys Asp Gly Pro Trp Ser Asp Cys Ile Asp Arg Tyr Pro Val
                    480                 485

TTT ATT CCC GAA GTT GTC AAA CTC                                1491
Phe Ile Pro Glu Val Val Lys Leu (2) INFORMATION FOR SEQ ID NO:4:

(i) SEQUENCE CHARACTERISTICS:
        (A) LENGTH: 497
        (B) TYPE:  amino acid
        (C) STRANDEDNESS: single
        (D) TOPOLOGY: linear (xi) SEQUENCE DESCRIPTION: SEQ ID NO: 4:

Met Pro Gln Ala Pro Met Pro Glu Phe Ser Ser Val Lys Leu Lys
1               5                   10                  15

Tyr Val Lys Leu Gly Tyr Gln Tyr Leu Val Asn His Phe Leu Ser Phe
                20                  25                  30

Leu Leu Ile Pro Ile Met Ala Ile Val Ala Val Glu Leu Leu Arg Met
            35                  40                  45

Gly Pro Glu Glu Ile Leu Asn Val Trp Asn Ser Leu Gln Phe Asp Leu
    50                  55                  60

Val Gln Val Leu Cys Ser Ser Phe Phe Val Ile Phe Ile Ser Thr Val
65                  70                  75                  80

Tyr Phe Met Ser Lys Pro Arg Thr Ile Tyr Leu Val Asp Tyr Ser Cys
                85                  90                  95

Tyr Lys Pro Pro Val Thr Cys Arg Val Pro Phe Ala Thr Phe Met Glu
                100                 105                 110

His Ser Arg Leu Ile Leu Lys Asp Lys Pro Lys Ser Val Glu Phe Gln
            115                 120                 125

Met Arg Ile Leu Glu Arg Ser Gly Leu Gly Glu Thr Cys Leu Pro
    130                 135                 140

Pro Ala Ile His Tyr Ile Pro Pro Thr Pro Thr Met Asp Ala Ala Arg
145                 150                 155                 160

Ser Glu Ala Gln Met Val Ile Phe Glu Ala Met Asp Asp Leu Phe Lys
                165                 170                 175
```

-continued

```
Lys Thr Gly Leu Lys Pro Lys Asp Val Asp Ile Leu Ile Val Asn Cys
            180                 185                 190

Ser Leu Phe Ser Pro Thr Pro Ser Leu Ser Ala Met Val Ile Asn Lys
            195                 200                 205

Tyr Lys Leu Arg Ser Asn Ile Lys Ser Phe Asn Leu Ser Gly Met Gly
            210                 215                 220

Cys Ser Ala Gly Leu Ile Ser Val Asp Leu Ala Arg Asp Leu Leu Gln
225                 230                 235                 240

Val His Pro Asn Ser Asn Ala Ile Ile Val Ser Thr Glu Ile Ile Thr
                245                 250                 255

Pro Asn Tyr Tyr Gln Gly Asn Glu Arg Ala Met Leu Leu Pro Asn Cys
            260                 265                 270

Leu Phe Arg Met Gly Ala Ala Ala Ile His Met Ser Asn Arg Arg Ser
            275                 280                 285

Asp Arg Trp Arg Ala Lys Tyr Lys Leu Ser His Leu Val Arg Thr His
            290                 295                 300

Arg Gly Ala Asp Asp Lys Ser Phe Tyr Cys Val Tyr Glu Gln Glu Asp
305                 310                 315                 320

Lys Glu Gly His Val Gly Ile Asn Leu Ser Lys Asp Leu Met Ala Ile
                325                 330                 335

Ala Gly Glu Ala Leu Lys Ala Asn Ile Thr Thr Ile Gly Pro Leu Val
            340                 345                 350

Leu Pro Ala Ser Glu Gln Leu Leu Phe Leu Thr Ser Leu Ile Gly Arg
            355                 360                 365

Lys Ile Phe Asn Pro Lys Trp Lys Pro Tyr Ile Pro Asp Phe Lys Leu
            370                 375                 380

Ala Phe Glu His Phe Cys Ile His Ala Gly Gly Arg Ala Val Ile Asp
385                 390                 395                 400

Glu Leu Gln Lys Asn Leu Gln Leu Ser Gly Glu His Val Glu Ala Ser
                405                 410                 415

Arg Met Thr Leu His Arg Phe Gly Asn Thr Ser Ser Ser Leu Trp
            420                 425                 430

Tyr Glu Leu Ser Tyr Ile Glu Ser Lys Gly Arg Met Arg Arg Gly Asp
            435                 440                 445

Arg Val Trp Gln Ile Ala Phe Gly Ser Gly Phe Lys Cys Asn Ser Ala
            450                 455                 460

Val Trp Lys Cys Asn Arg Thr Ile Lys Thr Pro Lys Asp Gly Pro Trp
465                 570                 475                 480

Ser Asp Cys Ile Asp Arg Tyr Pro Val Phe Ile Pro Glu Val Val Lys
                485                 490                 495

Leu
```

(2) INFORMATION FOR SEQ ID NO: 5:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 5:

GTGCTTTATA TATGTTTG                                        18

(2) INFORMATION FOR SEQ ID NO: 6:

(i) SEQUENCE CHARACTERISTICS:

```
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 6:

CGTCGGAGAG TTTTAATG                                                    18

(2) INFORMATION FOR SEQ ID NO: 7:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 7:

CTTCGATATC GGTTGTTG                                                    18

(2) INFORMATION FOR SEQ ID NO: 8:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO: 8:

AAATACCCTA ATCACATTTT GTAA                                             24

(2) INFORMATION FOR SEQ ID NO: 9:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO: 9:

TTTAAACAGA GAGAAATATT CTTA                                             24

(2) INFORMATION FOR SEQ ID NO: 10:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO: 10:

ATGCCTCAGG CACCGATGCC AGAG                                             24

(2) INFORMATION FOR SEQ ID NO: 11:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO: 11:

CAGCACGAGA AACTAAAAAA TACC                                             24

(2) INFORMATION FOR SEQ ID NO: 12:

(i) SEQUENCE CHARACTERISTICS:
        (A) LENGTH: 1951
```

(B) TYPE: nucleic acid
        (C) STRANDEDNESS: single
        (D) TOPOLOGY: linear (xi) SEQUENCE DESCRIPTION: SEQ ID NO: 12:

```
TAGTGCTTTA TATATGTTTG ATACTTCTGT TTGGCAATAT CAATCATAGT          50

AGAAAAGATA TGGACTTCAT TTGAGGTTTT TGGTGGATTG TGTCTATATG         100

TGAAATCATG GGATCTCAAG ATTTGTCTGC ATTCAGTTTC CAAGTCAAAC         150

ATCGTAACTA CTGTTTGATT TTCCCTCATG CTTGCAGTTT TCATGGATAT         200

CTCAAGATTT GTCTTCTTGC ACTTTCCAAG TCAAACATAA AGTAACTACT         250

GATTGATATT CCCTCGTGTA TTACCCTCTT TCAAATGACA CAATTGGGCC         300

CAAGTAGAGG AATTTCATAG TGAATTCAAA AGATTAACTG TATTCCACCG         350

TCGTATTTTG ATAACATTTA GTTATTCCTT TTCTTTTTTT TCTTCTGCAA         400

CAGTTTTTTT TTAATACATT TAGTGTTGGT TTGGTTCAAT GAAATATTAT         450

ATGTTACTTC TTTTTTTGGA AATAAATTAT TCATTCTTTC TACTATAAAA         500

GGAATTGTTC ATGCTTTTTT GATACAATAG TATACCATTT CAAAAGATAC         550

CATAGACCAG TTATTACATG AATCGCCAAA ACAACACTAA AATCAGAAAA         600

TCAGTATATT TTGGTATAGT CTCCAACATA CAATCATAAA ACCTCTGTGA         650

AATTTAAAAT CTATATTTGA CATTTCAAAG TTTAACAACA TAGTTCTAAA         700

TAATTACCTA AATTTTAAGT CAAATGTGAA TTATATTTTA CTCTTCGATA         750

TCGGTTGTTG ACGATTAACC ATGCAAAAAA GAAACATTAA TTGCGAATGT         800

AAATAACAAA ACATGTAACT CTTGTAGATA TACATGTATC GACATTTAAA         850

CCCGAATATA TATGTATACC TATAATTTCT CTGATTTTCA CGCTACCTGC         900

CACGTACATG GGTGATAGGT CCAAACTCAC AAGTAAAAGT TTACGTACAG         950

TGAATTCGTC TTTTTGGGTA TAAACGTACA TTTAATTTAC ACGTAAGAAA        1000

GGATTACCAA TTCTTTCATT TATGGTACCA GACAGAGTTA AGGCAAACAA        1050

GAGAAACATA TAGAGTTTTG ATATGTTTTC TTGGATAAAT ATTAAATTGA        1100

TGCAATATTT AGGGATGGAC ACAAGGTAAT ATATGCCTTT TAAGGTATAT        1150

GTGCTATATG AATCGTTTCG CATGGGTACT AAAATTATTT GTCCTTACTT        1200

TATATAAACA AATTCCAACA AAATCAAGTT TTTGCTAAAA CTAGTTTATT        1250

TGCGGGTTAT TTAATTACCT ATCATATTAC TTGTAATATC ATTCGTATGT        1300

TAACGGGTAA ACCAAACCAA ACCGGATATT GAACTATTAA AAATCTTGTA        1350

AATTTGACAC AAACTAATGA ATATCTAAAT TATGTTACTG CTATGATAAC        1400

GACCATTTTT GTTTTTGAGA ACCATAATAT AAATTACAGG TACGTGACAA        1450

GTACTAAGTA TTTATATCCA CCTTTAGTCA CAGTACCAAT ATTGCGCCTA        1500

CCGGGCAACG TGAACGTGAT CATCAAATCA AGTAGTTAC CAAACGCTTT         1550

GATCTCGATA AAACTAAAAG CTGACACGTC TTGCTGTTTC TTAATTTATT        1600

TCTCTTACAA CGACAATTTT GAGAAATATG AAATTTTTAT ATCGAAAGGG        1650

AACAGTCCTT ATCATTTGCT CCCATCACTT GCTTTTGTCT AGTTACAACT        1700

GGAAATCGAA GAGAAGTATT ACAAAAACAT TTTTCTCGTC ATTTATAAAA        1750

AAATGACAAA AAATTAAATA GAGAGCAAAG CAAGAGCGTT GGGTGACGTT        1800

GGTCTCTTCA TTAACTCCTC TCATCTACCC CTTCCTCTGT TCGCCTTTAT        1850
```

```
ATCCTTCACC TTCCCTCTCT CATCTTCATT AACTCATCTT CAAAAATACC          1900

CTAATCACAT TTTGTAACAA TAATACAATT ATACATTAAA ACTCTCCGAC          1950

G                                                              1951
```

NUCLEIC ACIDS ENCODING A PLANT ENZYME INVOLVED IN VERY LONG CHAIN FATTY ACID SYNTHESIS

PRIORITY CLAIM

This application claims priority to co-pending U.S. provisional patent application Ser. No. 60/043,831, filed on Apr. 14, 1997.

TECHNICAL FIELD

This invention relates to DNA molecules cloned from plants and methods of using such DNA molecules to produce transgenic plants with altered fatty acid composition.

BACKGROUND

Epicuticular waxes form the outermost layer of the aerial portion of the plant and are thus the first line of interaction between the plant and its environment. The physical properties of this wax layer protect the plant from numerous environmental stresses. For example, the hydrophobic nature of wax prevents dehydration (nonstomatal water loss) and aids in shedding rainwater. The reflective nature of wax protects the plant against UV radiation (Reicosky and Hanover, 1978). Waxes are also known to protect against acid rain (Percy and Baker, 1990) and, because they are a good solvent for organic pollutants, they are able to impede the uptake of aqueous foliar sprays (Schreiber and Schonherr, 1992). Furthermore, surface waxes protect plants from bacterial and fungal (Jenks et al., 1994) pathogens ad play a role in plant-insect interactions (Eigenbrode and Espelie, 1995). Recently it has been shown that some of the compounds found in epicuticular waxes are also present in the tryphine layer of pollen grains (Preuss et al., 1993). Without these compounds the tryphine layer erodes, resulting in pollen that is unable to function causing male sterility.

Epicuticular waxes are composed of long chain, hydrophobic compounds all derived from saturated very long chain fatty acids (VLCFAs), that are synthesized within and then secreted from the epidermis. VLCFAs are defined as those fatty acids whose chain length is 20 or more carbons long. The lengths will vary from plant to plant, but typically, the wax VLCFAs are approximately 26–34 carbon long. These VLCFAs are synthesized by a microsomal fatty acid elongation (FAE) system by sequential additions of C2 moieties from malonyl-coenzyme A (CoA) to pre-existing fatty acids derived from the de novo fatty acid synthesis (FAS) pathway of the plastid. Analogous to de novo FAS it is thought that each cycle of FAE involves four enzymatic reactions; (1) condensation of malonyl-CoA with a log chain acyl-CoA, (2) reduction to β-hydroxyacyl-CoA, (3) dehydration to an enoyl-CoA and (4) reduction of the enoyl-CoA, resulting in the elongated acyl-CoA (Fehling and Mukherjee, 1991). Together these four activities are termed the elongase (von Wettstein-Knowles, 1982). VLCFAs in the epidermis are then converted to the other wax components through a number of pathways consisting of multienzyme complexes. For example VLCFAs are converted to aldehydes by fatty acyl-CoA reductase (Kolattukudy, 1971). These aldehydes can either be reduced by aldehyde reductase to produce primary alcohols (Kolattukudy, 1971), or decarbonylated by an aldehyde decarbonylase to produce odd chained alkanes (Cheesbrough and Kolattukudy, 1984). Alkanes can then undergo oxidation to form firstly secondary alcohols and then ketones (for review see Post-Beittenmiller, 1996). Very little is known at the molecular level about the components that are involved in the biosynthesis of wax specific compounds and their secretion onto the plant surface. Genetic studies have shown that there are a large number of genes involved in these processes (for example, 22 loci have been reported in Arabidopsis, 84 in barley). However only a few of these genes have been isolated so far and the biochemical role of their gene products remains unknown (Lemieux, 1996).

In addition to being made in the epidermal cells, VLCFAs also accumulate in the seed oil of some plant species. To date, developing seeds have been the primary focus of research into VLCFA biosynthesis. In seeds VLCFAs are incorporated into triacylglyerols (TAGs), as in the Brassicaceae, or into wax esters, as in Jojoba. The seed VLCFAs include the agronomically important erucic acid (C22:1), with oils containing this fatty acid used in the manufacture of lubricants, nylon, cosmetics, pharmaceuticals and plasticisers (Battey et al., 1989); Johnston and Fritz, 1989). Conversely, VLCFAs have detrimental nutritional effects and are therefore undesirable in edible oils. This has led to the breeding of Canola rapeseed varieties that are almost devoid of VLCFAs (Stefansson et al., 1961).

The seeds of Arabidopsis contain approximately 28% [w/wt of total fatty acids (FA)] of VLCFAs, eicosenoic acid (20:1) being the predominant VLCFA (21% of wt/wt of total FA). To identify the gene products that are involved in the synthesis of seed VLCFAs and establish the VLCFA biosynthetic pathway, several groups performed mutational analysis and screened for seed that had reduced VLCFA content. Each group independently identified the FATTY ACID ELONGATION1 gene (FAE1; James and Dooner, 1990; Kunst et al., 1992; Lemieux et al., 1990). A mutation at this locus resulted in reduced VLCFA levels (<1% wt/wt of total FA) in the seed. Several other mutations that were non-allelic to FAE1 were also isolated. However, these mutations had a less pronounced effect in that VLCFAs still constituted 6.7% (wt/wt of total FA) of the seed fatty acid (Katavic et al., 1995; Kunst et al., 1992). Thus, despite the fact that four enzymatic activities are required for each elongation step, the FAE1 gene was the only one found by mutant analysis that resulted in almost complete loss of VLCFA synthesis in the seed.

The Arabidopsis FAEI gene was subsequently cloned (James et al., 1995; WO 96/13582), and showed homology to three condensing enzymes: chalcone synthase, stilbene synthase and β-ketoacyl-[acyl carrier protein] synthase III (17 amino acids were identical to a 50 amino acid region of a consensus sequence for condensing enzymes). Based on this homology it was proposed that FAE1 encodes a β-ketoacyl-coenzyme A synthase (KCS), the condensing enzyme which catalyzes the first reaction of the microsomal fatty acid elongation system (James et al., 1995). As determined by Northern analysis, the FAE1 gene is expressed in seeds of Arabidopsis, but is absent from leaves (James et al., 1995). This result is consistent with the fact that the faeI mutation affects only the fatty acid composition of the developing seed, having no pleiotropic effects on fatty acid composition of the vegetative, or floral parts of the plant. Thus, FAE1 is regarded as a seed-specific condensing enzyme.

Recently a cDNA from Jojoba seeds involved in the syntheses of VLCFAs has been isolated (Lassner et al., 1996; WO 95/15387). The protein encoded by this cDNA showed high homology to FAE1 (52% amino acid identity), and biochemical analysis demonstrated that it has a KCS activity. Using Jojoba KCS cDNA, Lassner et al. (1996) were able to complement the mutation in a Canola variety of *Brassica napus*, restoring a low erucic acid rapeseed line to a line that contained higher levels of VLCFAs. This suggests that in Canola, the mutation is in the structural gene encoding KCS, or a gene affecting KCS activity. Thus, both in Arabidopsis and *Brassica napus,* the mutations that result in the abolition of VLCFA synthesis seem to affect the condensing enzyme.

If four enzyme activities are necessary for an elongation step, and FAE1 and Jojoba-KCS only encode the KCS activity, one might expect to find other complementation groups that result in very low levels of VLCFAs synthesis. Because these complementation groups were not found in mutation screenings, Millar and Kunst (1997) have hypothesized that these three activities are not seed specific, but ubiquitously present throughout the plant and shared with other FAE systems involved in VLCFA formation including wax biosynthesis. To test this FAE1 was ecotopically expressed in yeast and in tissues of Arabidopsis and tobacco, where significant quantities of VLCFAs are not found. Expression of FAE1 alone in these cells resulted in the biosynthesis and accumulation of VLCFAs. This demonstrated that the condensing enzyme is the pivotal control point of the elongase, controlling not only the amounts of VLCFAs produced, but also their chain lengths. In contrast, it appears that the other three enzyme activities of the elongase are found ubiquitously throughout the plant, are not rate limiting and play no role in the control of VLCFA synthesis. The ability of yeast containing FAE1 to synthesize VLCFAs suggests that the expression, and the acyl chain length specificity of the condensing enzyme, along with the apparent broad specificities of the other three FAE activities, may be universal eukaryotic mechanism for regulating the amounts and acyl chain length of VLCFAs synthesized in any given cell (Millar and Kunst, 1997).

Thus, considering the central role of the condensing enzyme for VLCFA synthesis, the isolation of genes encoding condensing enzymes involved in the production of wax specific VLCFAs would facilitate the modification of wax composition through genetic engineering. Furthermore, since the majority of wax components are derived from VLCFAs, the availability of such genes would offer the potential to modify the wax load itself. This offers the potential to modify the susceptibility of plants to environmental stresses such as ultraviolet light, heat and drought, as well as the ability of plants to withstand insects and pathogens. The present invention is directed towards nucleic acids that encode condensing enzymes for VLCFA synthesis.

SUMMARY OF THE INVENTION

The present invention provides nucleic acids (cDNAs and genomic clones) that encode a key enzyme in the synthesis of VLCFAs in plant epidermal cells. The activity of this enzyme is referred to as very long chain fatty acid elongase; the activity is required for synthesis of VLCFAs of greater than 24 carbons in length. It is shown that co-suppression of the CUT1 gene in plants can disrupt VLCFA synthesis which results in plants having none of the protective wax usually found on stem surfaces. In addition, it is shown that such plants are conditionally male sterile: when grown under normal humidity, the plants are male sterile, but fertility can be restored by growth in an elevated humidity environment.

The invention thus provides the CUT1 cDNA and gene nucleotide sequences ("CUT1 nucleic acids") and the amino acid sequence of the CUT1 protein. In one embodiment, the CUT1 nucleic acids disclosed are from *Arabidopsis thaliana.* The open reading frame of the Arabidopsis CUT1 cDNA molecule encodes an enzyme of 497 amino acids which catalyzes the addition of 2C units to preexisting C24 or longer fatty acids.

Also encompassed within the scope of this invention are transformation vectors that include at least a portion of the CUT1 nucleic acid molecules. Such vectors may be transformed into plants to produce transgenic plants with modified VLCFA compositions (relative to non-transgenic plants of the same species). Depending on the particular sequences incorporated into the vector, transformation with the CUT1 cDNA, gene or derivatives thereof can be used to modify agronomically important traits, including the presence, composition and thickness of epicuticular wax layers on leaves and stems, seed coat fatty acids, seed oil composition and male sterility. Typically, such vectors include regulatory sequences, such as promoters, operably linked to the CUT1 open reading frame or a derivative of the CUT1 nucleic acids. For example, VLCFA synthesis may be altered by introducing into a plant a transformation vector that includes a sense or antisense version of the CUT1 cDNA. Transgenic plants having modified VLCFA compositions and which are transformed with such recombinant transformation vectors are also provided by this invention.

In one aspect of the invention, transformation with sense or antisense versions of the CUT1 nucleic acids may be used to produce plants having modified epicuticular wax layers on the aerial parts of the plants, such as the leaves and stems. A modified epicuticular wax layer may be modified in physical respects, such as thickness of the wax layer, or in composition. Because these layers play a role in the ability of plants to resist environmental stresses, such as drought and ultraviolet light, as well as insects and pathogens, transformation with vectors including forms of the CUT1 nucleic acids may be used to produce plants with particular agronomic advantages. Producing plants with modified epicuticular wax composition may be achieved by introducing into the plants a vector in which the CUT1 nucleic acid (or a derivative thereof) is operably linked to a promoter that directs expression of the open reading frame in the epidermal cells. The CaMV 35S promoter and the endogenous CUT1 gene promoter are examples of regulatory sequences that may be suitable for this purpose.

Agronomically important traits in addition to wax composition may also be modified using the CUT1 nucleic acids of the present invention. For example, the fatty acid composition of the seed coat and the fatty acid composition of seed oil may be modified by transforming plants with the CUT1 cDNA or derivatives thereof. Preferably, where it is desired to modify aspects of seed VLCFA composition, the introduced CUT1 nucleic acid sequence will be operably linked to a promoter known to direct expression in seed tissues. Seed-specific promoters include the napin promoter of *Brassica napus* (Lee et al., 1991). In addition, transformation with the CUT1 nucleic acids or derivatives thereof may be used to disrupt VLCFA synthesis in pollen, resulting in conditionally male sterile plants. Such plants are useful in plant breeding programs.

While the invention provides CUT1-encoding nucleic acids from Arabidopsis, it additionally encompasses homologs, orthologs and variants and derivatives of these sequences, as well as homologs, orthologs and variants of the CUT1 polypeptide sequence. Thus, in one aspect of the invention, nucleic acid molecules that comprise specified regions of these sequences are provided. Exemplary of such nucleic acid molecules are oligonucleotides that are useful as probes or primers to detect and amplify CUT1-encoding nucleic acids from other plant species. Such oligonucleotides are useful as hybridization probes or PCR primers, and typically comprise at least 15 consecutive bases of the disclosed CUT1 nucleic acid sequences. In other embodiments, such oligonucleotides comprise longer regions of the disclosed CUT1 sequences, such as at least 20, 25 or 30 consecutive nucleotides.

In another aspect, the invention provides compositions and methods for isolating nucleic acid sequences that encode enzymes having CUT1 activity from other plant species. Typically, such methods involve hybridizing probes or primers derived from the disclosed Arabidopsis sequences to nucleic acids obtained or derived from such other plant species.

Homologous and orthologous sequences to Arabidopsis CUT1 nucleic acid and CUT1 amino acid sequences share key functional and structural characteristics with the disclosed Arabidopsis sequences. Functionally, such sequences encode (or comprise) a polypeptide that catalyzes the very long chain fatty acid elongation as described above. Structurally, such sequences share a specified structural relationship with the disclosed sequences. By way of example, in certain embodiments, homologous amino acid sequences have at least 70% sequence identity with the Arabidopsis CUT1 amino acid sequence. In other embodiments, homologous nucleic acid sequences hybridize under stringent conditions to the disclosed Arabidopsis CUT1 nucleic acid sequences.

Another aspect of the invention relates to the purified CUT1 enzyme itself. Having provided nucleic acid molecules that encode this enzyme, the invention also facilitates the expression of CUT1 enzyme in heterologous systems, including *E. coli,* yeast and baculovirus expression systems. Thus, the invention permits the large scale production of the enzyme for agricultural and other applications.

In another aspect of the invention the promoter sequence of the CUT1 gene is disclosed. This promoter sequence confers epidermis-specific expression, and may be used to express a variety of nucleic acids in an epidermis-specific manner.

DETAILED DESCRIPTION OF THE INVENTION

I. Definitions

Unless otherwise noted, technical terms are used according to conventional usage. Definitions of common terms in molecular biology may be found in Benjamin Lewin, *Genes V* published by Oxford University Press, 1994 (ISBN 0-19-854287-9); Kendrew et al (eds.), *The Encyclopedia of Molecular Biology,* published by Blackwell Science Ltd., 1994 (ISBN 0-632-02182-9); and Robert A. Meyers (ed.), *Molecular Biology and Biotechnology: a Comprehensive Desk Reference,* published by VCH Publishers, Inc., 1995 (ISBN 1-56081-569-8). The nomenclature for DNA bases as set forth at 37 CFR §1.822 and the standard three letter codes for amino acid residues are used herein.

In order to facilitate review of the various embodiments of the invention, the following definitions of terms are provided:

CUT1 protein: The defining functional characteristic of a CUT1 protein is its enzymatic activity, specifically its very long chain fatty acid elongase activity. This activity is manifested as the catalysis of one or more steps in the addition of 2 carbon moieties (such as malonyl-coenzyme A) to pre-existing very long chain fatty acids (VLCFAs). In a preferred embodiment, a CUT1 protein catalyzes one or more steps in the addition of 2 carbon moieties to pre-existing long chain fatty acids of at least 24 carbon units in length. This activity can be measured by the assay described below.

This invention provides a cDNA and a gene encoding a CUT1 enzyme from *Arabidopsis thaliana.* However the invention is not limited to this particular CUT1 protein: other nucleotide sequences which encode CUT1 proteins are also part of the invention, including variants on the disclosed Arabidopsis cDNA and gene sequences and orthologous sequences from other plant species, including naturally occurring variants, such as sequences from other ecotypes, species and natural polymorphisms, the cloning of which is now enabled. Such sequences share the essential functional characteristic of encoding an enzyme having very long chain fatty acid elongase activity. Nucleic acid sequences that encode CUT1 proteins and the proteins encoded by such nucleic acids share not only this functional characteristic, but also a specified level of sequence similarity (or sequence identity), as addressed below. The concept of sequence identity can also be expressed in the ability of two sequences to hybridize to each other under stringent conditions.

Sequence identity: the similarity between two nucleic acid sequences, or two amino acid sequences is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well-known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biological Information (NCBI, Bethesda, Md.) and on the Internet, for use in connection with the sequence analysis programs blastp, blastn, blastx, tblastn and tblastx. It can be accessed at htp://www.ncbi.nlm.nih.gov/BLAST/. A description of how to determine sequence identity using this program is available at http://www.ncbi.nlm.nih.gov/BLAST/blast help.html.

Homologs of the Arabidopsis CUT1 protein are characterized by possession of at least 70% sequence identity counted over the full length alignment with the disclosed Arabidopsis CUT1 amino acid sequence using the NCBI Blast 2.0, gapped blastp set to default parameters. Such homologous peptides will more preferably possess at least 75%, more preferably at least 80% and still more preferably at least 90% or 95% sequence identity with the Arabidopsis CUT1 amino acid sequence determined by this method. When less than the entire sequence is being compared for sequence identity, homologs will possess at least 75% and more preferably at least 85% and more preferably still at least 90% or 95% sequence identity over short windows of 10–20 amino acids. Methods for determining sequence identity over such short windows are described at http://www.ncbi.nlm.nih.gov/BLAST/blast FAQs.html. Homologs having the sequence identities described above will, in some embodiments, also possess VLCFA elongase activity. One of skill in the art will appreciate that these sequence identity ranges are provided for guidance only; it is entirely possible that strongly significant homologs could be obtained that fall outside of the ranges provided. The present invention provides not only the peptide homologs are described above, but also nucleic acid molecules that encode such homologs.

Homologs of the Arabidopsis CUT1 cDNA and gene are similarly characterized by possession of at least 60% sequence identity counted over the full length alignment with the disclosed Arabidopsis cDNA or gene sequence using the NCBI Blast 2.0, gapped blastn set to default parameters. Such homologous nucleic acids will more preferably possess at least 70%, more preferably at least 80% and still more preferably at least 90% or 95% sequence identity determined by this method. When less than the entire sequence is being compared for sequence identity, homologs will possess at least 85% and more preferably at least 90% and more preferably still at least 95% sequence identity over 30 nucleotide windows. Homologs having the sequence identities described above will, in some embodiments, also encode a polypeptide having VLCFA elongase activity. However, homologs as defined above are useful for modifying VLCFA elongase activity in transgenic plants (for example, as used in antisense constructs) even when they do not encode a functional peptide. Again, one of skill in the art will appreciate that these sequence identity ranges are provided for guidance only; it is entirely possible that strongly significant nucleic acid homologs could be obtained that fall outside of the ranges provided.

Another indication that two nucleic acid molecules are substantially homologous is that the two molecules hybridize to each other under stringent conditions when one molecule is used as a hybridization probe, and the other is present in a biological sample, e.g., genomic material from a cell. Specific hybridization means that the molecules hybridize substantially only to each other and not to other molecules that may be present in the genomic material. Stringent conditions are sequence dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (1989) and Tijssen (1993). Hybridization conditions and stringencies are further discussed below.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequence that all encode substantially the same protein.

Probes and primers: Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987), and Innis et al., (1990). PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with its length. Thus, for example, a primer comprising consecutive nucleotides of the Arabidopsis CUT1 cDNA or gene will anneal to a target sequence (e.g., a corresponding CUT1 gene from *Zea mays*) with a higher specificity than a corresponding primer of only 15 nucleotides. Thus, in order to obtain greater specificity, probes and primers may be selected that comprise 20, 25, 30, 35, 40, 50 or more consecutive nucleotides of the Arabidopsis CUT1 cDNA or gene sequences. Such probes and primers are useful for obtaining CUT1 nucleic acid molecules (cDNA, genomic sequences, and portions of these molecules) both from Arabidopsis and other plant species.

Vector: A nucleic acid molecule as introduced into a host cell, thereby producing a transformed host cell. A vector may include nucleic acid sequences that permit it to replicate in the host cell, such as an origin of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, including transformation with Agrobacterium vectors, transfection with viral vectors, transformation with plasmid vectors, and introduction of naked DNA by electroporation, lipofection, and particle gun acceleration.

Isolated: An "isolated" biological component (such as a nucleic acid or protein) has been substantially separated or purified away from other biological components in the cell of the organism in which the component naturally occurs, i.e., other chromosomal and extrachromosomal DNA and RNA, and proteins. Nucleic acids and proteins which have been "isolated" thus include nucleic acids and proteins purified by standard purification methods. The term also embraces nucleic acids and proteins prepared by recombinant expression in a host cell as well as chemically synthesized nucleic acids.

Purified: The term purified does not require absolute purity; rather, it is intended as a relative term. Thus, for example, a purified CUT1 protein preparation is one in which the CUT1 protein is more enriched than the protein is in its natural environment within a cell. Preferably, a preparation of CUT1 protein is purified such that CUT1 protein represents at least 50% of the total protein content of the preparation.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter effects the transcription or expression of the coding sequence. Generally, operably linked DNA sequences are contiguous and, where necessary to join two protein coding regions, in the same reading frame.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Ortholog: two nucleotide or amino acid sequences are orthologs of each other if they share a common ancestral sequence and diverged when a species carrying that ancestral sequence split into two species. Orthologous sequences are also homologous sequences.

Transgenic plant: as used herein, this term refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant which contain the introduced DNA (whether produced sexually or asexually).

II. Sequence Listing and Figures

The nucleic and amino acid sequences listed in the accompanying sequence listing are showed using standard letter abbreviations for nucleotide bases, and three letter code for amino acids. Only one strand of each nucleic acid sequence is shown, but the complementary strand is understood to be included by any reference to the displayed strand.

Seq. I.D. No. 1 shows the nucleotide sequence of the CUT1 gene and the encoded amino acid sequence.

Seq. I.D. No. 2 shows the nucleotide sequence of the CUT1 cDNA.

Seq. I.D. No. 3 shows the nucleotide sequence of the CUT1 open reading frame.

Seq. I.D. No. 4 shows the amino acid sequence of the CUT1 protein.

Seq. I.D. Nos. 5–11 show primers useful in PCR amplification of various regions of the CUT1 gene, cDNA or ORF.

Seq. I.D. No. 12 shows the promoter region of the CUT1 genomic clone.

FIG. 1 shows the pathways of wax biosynthesis in Arabidopsis.

III. Isolation and Characterization of the CUT1 cDNA

The CUT1 cDNA was initially identified using a TBLASTN homology search (Altschul et al., 1990) of the database of expressed sequenced tags (ESTs) of anonymous Arabidopsis cDNA clones (Newman et al., 1994) using the deduced amino acid sequence of the FAE1 gene. The search found 14 ESTs in the database which had open reading frames with significant homology to FAE1. These ESTs did not correspond to known condensing enzymes such as chalcone synthase or 3-ketoacyl-acyl carrier protein synthase III.

One of these ESTs was selected for further investigation, and the corresponding full length cDNA was isolated. This cDNA is herein referred to as the CUT1 cDNA. Sequencing demonstrated that the CUT1 cDNA was 1829 nucleotides long, approximately the size of the FAE1 transcript (James et al., 1995). The CUT1 cDNA contains one open reading frame of 497 amino acids, which is shorter than both the FAE1 sequence (506 amino acids) and the jojoba KCS (521 amino acids). The CUT1 cDNA and the protein it encodes are shown in Seq. I.D. Nos. 2 and 4, respectively.

There is an in frame stop codon, TAA, 15 nucleotides upstream of the most 5' ATG, suggesting that this sequence indeed represents the full length amino acid sequence of the protein. Thus, the CUT1 cDNA as depicted in Seq. I.D. No. 2 has a 5' untranslated region of 58 nucleotides, an open reading frame of 1491 nucleotides and a 3' untranslated region of 258 nucleotides, excluding the poly(A) tail (22 As). Comparison of the deduced amino acid sequence of the CUT1 protein to FAE1 revealed that they are 50.0% identical and 74.7% similar.

IV. Isolation and Characterization of the CUT1 Gene

An Arabidopsis CUT1 genomic clone was isolated from a genomic library in λGEM11 by probing nitrocellulose plaque lifts with a full-length CUT1 cDNA clone. A 2.5 kb long SalI fragment containing 580 bp of the coding sequence and 1951 bp of the 5' upstream region was subcloned into the SalI site of pT7T3 18U plasmid (Pharmacia), followed by complete sequencing on both strands. The sequence of this genomic clone is shown in Seq. I.D. No. 1.

In situ hybridization studies in developing shoots, leaves and siliques of Arabidopsis indicated epidermis-specific expression of the CUT1 gene, as expected of a gene encoding an enzyme involved in wax biosynthesis.

V. Analysis of the CUT1 Promoter

In order to confirm the tissue and cell specificity of the CUT1 promoter, 5' flanking sequences from the CUT1 genomic clone were operably linked to the uidA reporter gene encoding β-glucuronidase (GUS). Two constructs were made, one having a 1.9 kb promoter fragment and the second containing a truncated 1.2 kb promoter. These promoter-GUS fusions were introduced into Arabidopsis and tobacco by Agrobacterium-mediated transformation and the promoter function characterized in transgenic plants.

To obtain the 1.9 and 1.2 kb regions of the CUT1 promoter sequence, synthetic oligonucleotides homologous to portions of the 5' untranslated region of the genomic clone were used as primers to amplify either a 1949 bp or a 1209 bp promoter fragment by PCR. As shown in FIG. 1, the upstream primer was 5'-GTGCTTTATATATGTTTG-3' (cutpro3) (Seq. I.D. No. 5) in combination with the downstream primer 5'-CGTCGGAGAGTTTTAATG-3' (cutpro1) (Seq. I.D. No. 6) for the PCR-synthesis of the 1949 bp fragment, and 5'-CTTCGATATCGGTTGTTG-3' (cutpro2) (Seq. I.D. No. 7) and cutpro1 for the amplification of the 1209 bp fragment. In both cases, the amplified products were subcloned in the HincII site of the plasmid pT7T318U (Pharmacia). The inserts were then cleaved out with HindIII and XbaI and directionally subcloned into the corresponding sites of the binary Ti plasmid pBI101 (Clontech), which contains a promoterless GUS gene (Jefferson et al. 1987). The pCUT1-GUS fusion constructs in pBI101 were introduced into *Agrobacterium tumefaciens* strain GV3101 (Koncz and Schell, 1986) by electroporation and selected for resistance to kanamycin (50 µg/ml).

For transformation of tobacco, Agrobacterium harbouring the pCUT1-GUS construct was co-cultivated with leaf pieces of *Nicotiana tabacum* SR1 and transformants were selected with kanamycin (100 mg/mL) on solid medium (Lee and Douglas, 1996). *Arabidopsis thaliana* (L.) Heynh. ecotype Columbia was transformed with pCUT1-GUS binary vector using a combination of in planta (Chang et al., 1994, Katavic et al., 1994) and vacuum infiltration methods (Bechtold et al., 1993). Plants were grown until the primary inflorescence shoots reached 1–2 cm in height, when this bolts were cut off. The wound site was inoculated with 50 mL of an overnight Agrobacterium culture. After 4–6 days a number of secondary inflorescences that appeared were cut off, and vacuum infiltration was performed on these plants using the conditions described by Bechtold et al. (1993). Screening for transformed seed was done on 50 µg/mL kanamycin as described previously (Katavic et al., 1994).

Tissue sections of transgenic plants containing the pCUT1-GUS constructs were placed in 100 mM $NaPO_4$ (pH7) and 1 mM spermidine for 15 min, then incubated at 37° C. in 0.5 $K_3[Fe(CN)_6]$, 0.01% Triton X-100, 1 mM EDTA, 10 mM β-mercaptoethanol, 5-bromo-4-chloro-3-indolyl-β-D-glucuronide in 100 mM $NaPO_4$ (pH7), until a blue color appeared (after approximately 1 hr). Following incubation with the substrate, chlorophyll was removed from the sections using a graded ethanol series.

In both recipient plant species, Arabidopsis and tobacco, CUT1 expression pattern mirrored that observed in the in situ experiments. Furthermore, both long and short CUT1 promoter fragments targeted expression of the uidA gene exclusively to the epidermis. No GUS expression was detected in any of the other cell types in the stems or leaves of transgenic plants. Thus, the Arabidopsis CUT1 promoter is regulated in a tissue specific, and cell specific manner, and epidermis specificity appears to be retained even in unrelated plant species like tobacco. In addition, no differences in the strength of expression were detected between the 1.9 kb and 1.2 kb promoter.

VI. Preferred Methods for Producing CUT1 Nucleic Acids

With the provision of the CUT1 cDNA and gene (the "CUT1 nucleic acids") the polymerase chain reaction (PCR) may now be utilized in a preferred method for producing the CUT1 nucleic acids. PCR amplification of the CUT1 cDNA sequence may be accomplished either by direct PCR from a plant cDNA library or by Reverse-Transcription PCR (RT-PCR) using RNA extracted from plant cells as a template. Methods and conditions for both direct PCR and RT-PCR are known in the art and are described in Innis et al. (1990). Suitable plant cDNA libraries for direct PCR include the Arabidopsis cDNA library described by Newman et al. (1994). Similarly, the CUT1 genomic sequence may be amplified directly from genomic DNA extracted from plants, or from plant genomic DNA libraries. Amplification may be used to obtain the full length cDNA or genomic sequence, or may be used to amplify selected portions of these molecules (for example for use in antisense constructs).

The selection of PCR primers will be made according to the portions of the CUT1 nucleic acids which are to be amplified. Variations in amplification conditions may be required to accommodate primers of differing lengths; such considerations are well known in the art and are discussed in Innis et al. (1990), Sambrook et al. (1989), and Ausubel et al. (1987). By way of example only, the entire CUT1 cDNA molecule as shown in Seq. I.D. No. 2 may be amplified using the following combination of primers:

primer 1 5' AAATACCCTAATCACATTTTGTAA 3' (Seq. I.D. No. 8)
primer 2 5' TTTAAACAGAGAGAAATATTCTTA 3' (Seq. I.D. No. 9)

The open reading frame portion of the cDNA may be amplified using the following primer pair:

primer 3 5' ATGCCTCAGGCACCGATGCCAGAG 3' (Seq. I.D. No. 10)
primer 4 5' CAGCACGAGAAACTAAAAAATACC 3' (Seq. I.D. No. 11)

These primers are illustrative only; it will be appreciated by one skilled in the art that many different primers may be derived from the provided sequences in order to amplify particular regions of the CUT1 sequences. Resequencing of PCR products obtained by these amplification procedures is recommended; this will facilitate confirmation of the amplified CUT1 sequence and will also provide information on natural variation on this sequence in different ecotypes and plant populations.

Oligonucleotides which are derived from the CUT1 nucleic acid sequences and which are suitable for use as PCR primers to amplify the CUT1 nucleic acid sequences are encompassed within the scope of the present invention. Preferably, such oligonucleotide primers will comprise a sequence of 15–20 consecutive nucleotides of the CUT1 nucleic acid sequences. To enhance amplification specificity, primers comprising at least 20–30 consecutive nucleotides of these sequences may also be used.

VII. Cloning CUT1 Variants

With the provision herein of the CUT1 nucleic acid sequences, the cloning by standard methodologies of corresponding cDNAs and genes from other ecotypes and plant species, as well as polymorphic forms of the disclosed sequences is now enabled. Thus, the present invention includes methods of isolating a nucleotide sequence encoding a plant very long chain fatty acid elongation enzyme from a plant. Both conventional hybridization and PCR amplification procedures may be utilized to clone such sequences. Common to both of these techniques is the hybridization of probes or primers derived from the disclosed CUT1 nucleic acid sequences to a target nucleotide preparation, which may be, in the case of conventional hybridization approaches, a cDNA or genomic library or, in the in the case of PCR amplification, extracted genomic DNA, mRNA, a cDNA library or a genomic library.

Direct PCR amplification may be performed on cDNA libraries prepared from the plant species in question, or RT-PCR may be performed using mRNA extracted from the plant cells using standard methods. PCR primers will comprise at least 15 consecutive nucleotides of the CUT1 nucleic acid sequences. One of skill in the art will appreciate that sequence differences between the disclosed CUT1 nucleic acid sequences and the target gene to be amplified may result in lower amplification efficiencies. To compensate for this, longer PCR primers or lower annealing temperatures may be used during the amplification cycle. Where lower annealing temperatures are used, sequential rounds of amplification using nested primer pairs may be necessary to enhance specificity.

For conventional hybridization techniques, the hybridization probe is preferably labeled with a detectable label such as a radioactive label, and the probe is of at least 20 nucleotides in length. As is well known in the art, increasing length of hybridization probes tends to give enhanced specificity. The labeled probe derived from, for example, the CUT1 cDNA sequence may be hybridized to a plant cDNA or genomic library and the hybridization signal detected using means known in the art. The hybridizing colony or plaque (depending on the type of library used) is then purified and the cloned sequence contained in that colony or plaque isolated and characterized.

VIII. Use of the CUT1 Nucleic Acids to Produce Plants with Modified VLCFA Composition Once a gene or cDNA ("nucleic acid") encoding a protein involved in the determination of a particular plant characteristic has been isolated, standard techniques may be used to express the nucleic acid in transgenic plants in order to modify that particular plant characteristic. The basic approach is to clone the nucleic acid into a transformation vector, such that it is operably linked to control sequences (e.g., a promoter) which direct expression of the open reading frame in plant cells. The transformation vector is then introduced into plant cells by one of a number of techniques (e.g., electroporation) and progeny plants containing the introduced nucleic acid are selected. Preferably all or part of the transformation vector will stably integrate into the genome of the plant cell. That part of the transformation vector which integrates into the plant cell and which contains the introduced nucleic acid and associated sequences for controlling expression (the introduced "transgene") may be referred to as the recombinant expression cassette.

Selection of progeny plants containing the introduced transgene may be made based upon the detection of an altered phenotype. Such a phenotype may result directly from the nucleic acid cloned into the transformation vector or may be manifested as enhanced resistance to a chemical agent (such as an antibiotic) as a result of the inclusion of a dominant selectable marker gene incorporated into the transformation vector.

The choice of (a) control sequences and (b) how the nucleic acid (or selected portions of the nucleic acid) are arranged in the transformation vector relative to the control sequences determine, in part, how the plant characteristic affected by the introduced nucleic acid is modified. For example, the control sequences may be tissue specific, such that the nucleic acid is only expressed in particular tissues of the plant (e.g., pollen) and so the affected characteristic will be modified only in those tissues. The nucleic acid sequence may be arranged relative to the control sequence such that the nucleic acid transcript is expressed normally, or in an antisense orientation. Expression of an antisense RNA corresponding to the cloned nucleic acid will result in a reduction of the targeted gene product (the targeted gene product being the protein encoded by the plant gene from which the introduced nucleic acid was derived). Overexpression of the introduced nucleic acid, resulting from a plus-sense orientation of the nucleic acid relative to the control sequences in the vector, may lead to an increase in the level of the gene product, or may result in co-suppression (also termed "sense suppression") of that gene product.

Successful examples of the modification of plant characteristics by transformation with cloned nucleic acid sequences are replete in the technical and scientific literature. Selected examples, which serve to illustrate the current knowledge in this field of technology, and which are herein incorporated by reference, include:

U.S. Pat. No. 5,451,514 to Boudet (modification of lignin synthesis using antisense RNA and co-suppression);

U.S. Pat. No. 5,443,974 to Hitz (modification of saturated and unsaturated fatty acid levels using antisense RNA and co-suppression);

U.S. Pat. No. 5,530,192 to Murase (modification of amino acid and fatty acid composition using antisense RNA);

U.S. Pat. No. 5,455,167 to Voelker (modification of medium chain fatty acids)

U.S. Pat. No. 5,231,020 to Jorgensen (modification of flavonoids using co-suppression);

U.S. Pat. No. 5,583,021 to Dougherty (modification of virus resistance by expression of plus-sense untranslatable RNA);

WO 96/13582 (modification of seed VLCFA composition using over expression, co-suppression and antisense RNA in conjunction with the Arabidopsis FAE1 gene); and WO 95/15387 (modification of seed VLCFA composition using over expression of jojoba wax synthesis gene).

These examples include descriptions of transformation vector selection, transformation techniques and the construction of constructs designed to over-express the introduced nucleic acid or to express antisense RNA corresponding to the nucleic acid. In light of the foregoing and the provision herein of the CUT1 nucleic acids, it is thus apparent that one of skill in the art will be able to introduce these nucleic acids, or derivative forms of these molecules (e.g., antisense forms), into plants in order to produce plants having modified VLCFA compositions. Examples one and two below provides illustrations of this in which the CUT1 cDNA is operably linked to the CaMV 35S promoter sequence, cloned into the pBIN19 transformation vector and introduced into Arabidopsis using a vacuum infiltration method.

As reported in Example one, certain of the plants transformed in this way had no detectable epicuticular wax layers, indicating that transformation with the CUT1 cDNA had disrupted normal VLCFA synthesis in the plant epidermal cells. Such disruption is likely attributable to the phenomenon termed co-suppression (or sense-suppression). These plants are thus referred to as "CUT1-suppressed". This phenomenon may be affected by factors such as positional location of the introduced sequences in the plant genome.

Over-expression of CUT1 protein in transgenic plants, resulting in plants enhanced epicuticular wax layers will be a useful agronomic trait, providing increased drought and insect resistance. For example, drought resistance in rice is associated with high wax lines rich in $C_{29}$, $C_{33}$ and $C_{35}$ alkanes (O'Toole and Cruz, 1983; Haque et al., 1992). Increased wax deposition in transgenic plants can be accomplished by overexpression of CUT1 protein, while the identification of the CUT1 promoter allows targeting of lipid modification enzymes such as desaturases, thioesterases and other condensing enzymes with different specificities to the epidermal cells to modify wax composition.

Transformation of plants with the CUT1 nucleic acids or derivatives thereof may be used to modify other plant characteristics, such as seed coat composition and seed oil composition. Because condensing enzymes are pivotal enzymes in the synthesis of VLCFAs, controlling levels of accumulation of VLCFAs and their acyl chain length (Millar and Kunst, 1997) through the manipulation of CUT1 expression will permit the production of plants having novel fatty acid compositions. For instance, the accumulation of VLCFAs in tobacco seed expressing FAE1 from Arabidopsis (Millar and Kunst, 1997) raises the possibility of producing VLCFAs in plant species that currently do not synthesize VLCFAs. In addition, targeting of CUT1 to seeds will be useful to produce crop plants capable of synthesising new, agronomically important VLCFAs in seed oil.

Disruption of CUT1 activity in transgenic plants also provides a simple means for obtaining conditional male sterility in plants (see Example two). One of the major factors contributing to increases in crop productivity is the development of hybrid varieties of crops. Several different breeding strategies have been used to produce hybrid seed, but none of these strategies can be used as a general approach in all crop plants (Goldberg et al.,1993). As an alternative, genetically engineered systems and strategies for male fertility control that are applicable to a wide range of crops have recently been developed. For example, nuclear male sterility has been engineered by (1) tapetum-specific expression of a bacterial RNAse gene (Mariani et al., 1990, 1992), (2) overexpression of the rolC gene from *Agrobacterium rhizogenes* (Fladung, 1990; Schmüllhing et al., 1988, 1992), (3) expression of glucanase that disrupts the callose wall of the microsporophyte prematurely (Tsuchiya et al., 1995; Worrall et al., 1992), (4) the inhibition of flavonoid biosynthetic genes like chalcone synthase and dihydroflavolon 4-reductase (van der Krol et al., 1988, 1990; van der Meer et al, 1992; Napoli et al. 1990; Taylor and Jorgensen, 1992), and (5) altered expression of stilbene synthase (Fischer et al., 1997). However, in most of these cases the restoration of fertility is not simple, or not easily controlled. In contrast, conditional male sterility caused by suppression of CUT1 activity is easily reversible under high relative humidity.

The selection of vectors and promoters appropriate for targeting particular characteristics for modification (such as seed-specific expression) are well known; the following paragraphs set forth general guidance on the various options available in producing transgenic plants having modified VLCFA composition.

a. Plant Types

VLCFAs are found in all plant types, and thus DNA molecules according to the present invention (e.g., the CUT1 cDNA, gene, homologs and antisense forms thereof) may be introduced into any plant type in order to modify the VLCFA composition of the plant. Thus, the sequences of the present invention may be used to modify VLCFA composition in any higher plant, including monocotyledonous and dicotyledenous plants, including, but not limited to maize, wheat, rice, barley, soybean, beans in general, rape/canola, alfalfa, flax, sunflower, safflower, brassica, cotton, flax, peanut, clover; vegetables such as lettuce, tomato, cucurbits, potato, carrot, radish, pea, lentils, cabbage, broccoli, brussel sprouts, peppers; tree fruits such as apples, pears, peaches, apricots; flowers such as carnations and roses.

b. Vector Construction, Choice of Promoters

A number of recombinant vectors suitable for stable transfection of plant cells or for the establishment of transgenic plants have been described including those described in Pouwels et al., (1987), Weissbach and Weissbach, (1989), and Gelvin et al., (1990). Typically, plant transformation vectors include one or more cloned plant genes (or cDNAs) under the transcriptional control of 5' and 3' regulatory sequences and a dominant selectable marker. Such plant transformation vectors typically also contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Examples of constitutive plant promoters which may be useful for expressing CUT1 nucleic acids include: the cauliflower mosaic virus (CaMV) 35S promoter, which confers constitutive, high-level expression in most plant tissues (see, e.g., Odel et al., 1985, Dekeyser et al., 1990, Terada and Shimamoto, 1990); the nopaline synthase promoter (An et al., 1988); and the octopine synthase promoter (Fromm et al., 1989).

A variety of plant gene promoters that are regulated in response to environmental, hormonal, chemical, and/or developmental signals, also can be used for expression of CUT1 nucleic acids in plant cells, including promoters regulated by: (a) heat (Callis et al., 1988); (b) light (e.g., the pea rbcS-3A promoter, Kuhlemeier et al., 1989, the maize rbcS promoter, Schaffner and Sheen, 1991, and the chlorophyll a/b binding protein promoter, Simpson et al., 1985); (c) hormones, such as abscisic acid (Marcotte et al., 1989); (d) wounding (e.g., wunI, Siebertz et al., 1989); and (e) chemicals such as methyl jasmonate or salicylic acid. It may also be advantageous to employ tissue-specific promoters, such as those described by Roshal et al., (1987), Schernthaner et al., (1988), and Bustos et al., (1989).

Alternatively, tissue specific (root, leaf, flower, and seed for example) promoters (Carpenter et al. 1992, Denis et al. 1993, Opperman et al. 1993, Stockhause et al. 1997; Roshal et al., 1987; Schernthaner et al., 1988; and Bustos et al., 1989) can be fused to the coding sequence to obtained particular expression in respective organs. In addition, the timing of the expression can be controlled by using promoters such as those acting at senescencing (Gan and Amasino 1995) or late seed development (Odell et al. 1994). The promoter region of the CUT1 genomic sequence disclosed herein confers epidermis-specific expression in Arabidopsis and tobacco. Accordingly, the native promoter may be used to obtain epidermis-specific expression of the introduced transgene.

For producing conditionally male sterile plants by blocking CUT1 activity in pollen, it is preferable to use a pollen-specific promoter (so as to avoid pleiotropic effects). Thus, the CUT1 coding region may be expressed under the control of the tapetum-specific promoters such as TA29 (Mariani et al.,1990, 1992), MS2 (Aarts et al., 1997), and tap1 (Nacken et al., 1991).

Plant transformation vectors may also include RNA processing signals, for example, introns, which may be positioned upstream or downstream of the CUT1 nucleic acid sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Finally, as noted above, plant transformation vectors may also include dominant selectable marker genes to allow for the ready selection of transformants. Such genes include those encoding antibiotic resistance genes (e.g., resistance to hygromycin, kanamycin, bleomycin, G418, streptomycin or spectinomycin) and herbicide resistance genes (e.g., phosphinothricin acetyltransferase).

c. Arrangement of CUT1 Nucleic Acids in Vector

As noted above, the particular arrangement of the CUT1 nucleic acid in the transformation vector will be selected according to the expression of the nucleic acid desired.

Where enhanced VLCFA synthesis is desired, the CUT1 nucleic acid may be operably linked to a constitutive high-level promoter such as the CaMV 35S promoter. Modification of VLCFA synthesis may also be achieved by introducing into a plant a transformation vector containing a variant form of the CUT1 nucleic acid, for example a form which varies from the exact nucleotide sequence of the CUT1 nucleic acid, but which encodes a protein that retains the functional characteristic of the CUT1 protein, i.e., very long chain fatty acid elongation activity.

In contrast, a reduction of VLCFA synthesis may be obtained by introducing antisense constructs based on the CUT1 nucleic acid sequence into plants. For antisense suppression, the CUT1 nucleic acid is arranged in reverse orientation relative to the promoter sequence in the transformation vector. The introduced sequence need not be the full length CUT1 nucleic acid, and need not be exactly homologous to the CUT1 nucleic acid. Generally, however, where the introduced sequence is of shorter length, a higher degree of homology to the native CUT1 sequence will be needed for effective antisense suppression. Preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides.

Transcription of an antisense construct as described results in the production of RNA molecules that are the reverse complement of mNRA molecules transcribed from the endogenous CUT1 gene in the plant cell. Although the exact mechanism by which antisense RNA molecules interfere with gene expression has not been elucidated, it is believed that antisense RNA molecules bind to the endogenous mRNA molecules and thereby inhibit translation of the endogenous mRNA.

Suppression of endogenous CUT1 gene expression can also be achieved using ribozymes. Ribozymes are synthetic RNA molecules that possess highly specific endoribonuclease activity. The production and use of ribozymes are disclosed in U.S. Pat. Nos. 4,987,071 to Cech and 5,543,508 to Haselhoff, which are hereby incorporated by reference. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Constructs in which the CUT1 nucleic acid (or variants thereon) are over-expressed may also be used to obtain co-suppression of the endogenous CUT1 gene in the manner described in U.S. Pat. No. 5,231,021 to Jorgensen. Such co-suppression (also termed sense suppression) does not require that the entire CUT1 nucleic acid be introduced into the plant cells, nor does it require that the introduced sequence be exactly identical to the CUT1 nucleic acid. However, as with antisense suppression, the suppressive efficiency will be enhanced as (1) the introduced sequence is lengthened and (2) the sequence similarity between the introduced sequence and the endogenous CUT1 gene is increased. Example I below provides an illustration of co-suppression of the endogenous CUT1 gene by transformation of plants with the CUT1 cDNA.

d. Transformation and Regeneration Techniques

Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene mediated transformation; transformation using viruses; micro-injection of plant cells; micro-projectile bombardment of plant cells; vacuum infiltration; and *Agrobacterium tumeficiens* (AT) mediated transformation. Typical procedures for transforming and regenerating plants are described in the patent documents listed at the beginning of this section.

e. Selection of Transformed Plants

Following transformation and regeneration of plants with the transformation vector, transformed plants are preferably selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic. Example I provides an example of such an approach in which seedlings were selected using kanamycin.

After transformed plants are selected and grown to maturity, they can be assayed to determine whether VLCFA synthesis has been altered as a result of the introduced transgene. This can be done in several ways, including, as described in Example 1, microscopic examination of the epicuticular wax layer and chromatographic analysis. Lipids may also be extracted from plant material and analyzed by gas chromatography as described by Dooner (1990). In addition, antisense or sense suppression of the endogenous CUT1 gene may be detected by analyzing mNRA expression on Northern blots.

IX. Production of Sequence Variants

As noted above, modification of VLCFA synthesis in plant cells can be achieved by transforming plants with CUT1 nucleic acids, antisense constructs based on CUT1 nucleic acid sequences or other variants on CUT1 nucleic acid sequences. With the provision of the CUT1 cDNA and genomic sequences herein, the creation of variants on these CUT1 nucleic acid sequences by standard mutagenesis techniques is now enabled.

Variant DNA molecules include those created by standard DNA mutagenesis techniques, for example, M13 primer mutagenesis. Details of these techniques are provided in Sambrook et al. (1989), Ch. 15. By the use of such techniques, variants may be created which differ in minor ways from the disclosed CUT1 nucleic acids. DNA molecules and nucleotide sequences that are derivatives of those specifically disclosed herein and which differ from those disclosed by the deletion, addition or substitution of nucleotides while still encoding a protein which possesses the functional characteristic of the CUT1 protein (i.e., very long chain fatty acid elongation activity) are comprehended by this invention. DNA molecules and nucleotide sequences which are derived from the CUT1 nucleic acids include DNA sequences which hybridize under moderately stringent conditions to the DNA sequences disclosed, or fragments thereof.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (1989), chapters 9 and 11, herein incorporated by reference. By way of illustration only, a hybridization experiment may be performed by hybridization of a CUT1-derived probe (for example, the CUT1 cDNA sequence) to a target DNA molecule (for example, the CUT1 homolog from *Zea Mays*) which has been electrophoresed in an agarose gel and transferred to a nitrocellulose membrane by Southern blotting (Southern, 1975), a technique well known in the art and described in (Sambrook et al., 1989). Hybridization with a target probe labeled with $[^{32}P]$-dCTP is generally carried out in a solution of high ionic strength such as 6×SSC at a temperature that is 20–25° C. below the melting temperature, $T_m$, described below. For such Southern hybridization experiments where the target DNA molecule on the Southern blot contains 10 ng of DNA or more, hybridization is typically carried out for 6–8 hours using 1–2 ng/ml radiolabeled probe (of specific activity equal to $10^9$ CPM/μg or greater). Following hybridization, the nitrocellulose filter is washed to remove background hybridization. The washing conditions should be as stringent as possible to remove background hybridization but to retain a specific hybridization signal. The term $T_m$ represents the temperature above which, under the prevailing ionic conditions, the radiolabeled probe molecule will not hybridize to its target DNA molecule. The $T_m$ of such a hybrid molecule may be estimated from the following equation (Bolton and McCarthy, 1962):

$$T_m = 81.5°\ C. - 16.6(\log_{10}[Na^+]) + 0.41(\%G+C) - 0.63(\%\ \text{formamide}) - (600/1)$$

Where l=the length of the hybrid in base pairs.

This equation is valid for concentrations of $Na^+$ in the range of 0.01 M to 0.4 M, and it is less accurate for calculations of $T_m$ in solutions of higher $[Na^+]$. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al., 1989).

Thus, by way of example, for a 150 base pair DNA probe derived from the first 150 base pairs of the open reading frame of the CUT1 cDNA (with a hypothetical %GC=45%), a calculation of hybridization conditions required to give particular stringencies may be made as follows:

For this example, it is assumed that the filter will be washed in 0.3×SSC solution following hybridization, thereby $[Na^+]=0.045M$, %GC=45%, Formamide concentration=0, l=150 base pairs, $$T_m = 81.5 - 16(\log_{10}[Na^+]) + (0.41\times 45) - (600/150)$$

and so $$T_m = 74.4°\ C.$$

The $T_m$ of double-stranded DNA decreases by 1–1.5° C. with every 1% decrease in homology (Bonner et al., 1973). Therefore, for this given example, washing the filter in 0.3×SSC at 59.4–64.4° C. will produce a stringency of hybridization equivalent to 90%. Alternatively, washing the hybridized filter in 0.3×SSC at a temperature of 65.4–68.4° C. will yield a hybridization stringency of 94%. The above example is given entirely by way of theoretical illustration. One skilled in the art will appreciate that other hybridization techniques may be utilized and that variations in experimental conditions will necessitate alternative calculations for stringency.

DNA sequences that encode a protein having VLCFA elongase activity and which hybridize to the disclosed CUT1 nucleic acid sequences under hybridization conditions of at least 75%, more preferably at least 80%, 85% or 90% stringency, and most preferably at least 95% stringency are encompassed within the present invention.

The degeneracy of the genetic code further widens the scope of the present invention as it enables major variations in the nucleotide sequence of a DNA molecule while maintaining the amino acid sequence of the encoded protein. For example, the fourth amino acid residue of the CUT1 protein is alanine. This is encoded in the CUT1 ORF by the nucleotide codon triplet GCA. Because of the degeneracy of the genetic code, three other nucleotide codon triplets— GCT, GCC and GCG—also code for alanine. Thus, the nucleotide sequence of the CUT1 ORF could be changed at this position to any of these three codons without affecting the amino acid composition of the encoded protein or the characteristics of the protein. Based upon the degeneracy of the genetic code, variant DNA molecules may be derived from the CUT1 nucleic acid molecules disclosed herein using standard DNA mutagenesis techniques as described above, or by synthesis of DNA sequences. Thus, this invention also encompasses DNA sequences which encode the CUT1 protein but which vary from the CUT1 nucleic acid sequences by virtue of the degeneracy of the genetic code.

One skilled in the art will recognize that DNA mutagenesis techniques may be used not only to produce variant DNA molecules, but will also facilitate the production of proteins which differ in certain structural aspects from the CUT1 protein, yet which proteins are clearly derivative of this protein and which maintain the essential characteristics of the CUT1 protein. Newly derived proteins may also be selected in order to obtain variations on the characteristic of the CUT1 protein, as will be more fully described below. Such derivatives include those with variations in amino acid sequence including minor deletions, additions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Amino acid substitutions are typically of single residues; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mNRA structure.

Substitutional variants are those in which at least one residue in the amino acid sequence has been removed and a different residue inserted in its place. Such substitutions generally are made in accordance with the following Table 1 when it is desired to finely modulate the characteristics of the protein. Table 1 shows amino acids which may be substituted for an original amino acid in a protein and which are regarded as conservative substitutions.

TABLE 1

| Original Residue | Conservative Substitutions |
| --- | --- |
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in enzymatic function or other features are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of the CUT1 protein by analyzing the ability of the derivative proteins to catalyze the addition of C2 units to existing VLCFA units. These assays may conveniently be performed using the yeast-based systems for assaying fatty acid elongation described below.

X. Production of Recombinant CUT1 Protein Using Heterologous Expression Systems

Many different expression systems are available for expressing cloned nucleic acid molecules. Examples of prokaryotic and eukaryotic expression systems that are routinely used in laboratories are described in Chapters 16–17 of Sambrook et al. (1989), which are herein incorporated by reference. Such systems may be used to express CUT1 protein and derivatives at this protein at high levels to facilitate purification and functional analysis of the enzyme. Apart from permitting the activity of the enzyme to be determined (which is particularly useful to assess the activity of homologous and derivative proteins), heterologous expression facilitates other uses of the purified enzyme. For example the purified enzyme produced by recombinant means may be used to synthesize VLCFAs and other fatty acid metabolites in vitro, particularly radio- or fluorescent-labeled forms of VLCFAs and metabolites. These molecules may be used as tracers to determine the location in plant tissues and cells of VLCFAs and their metabolites. The purified recombinant enzyme may also be used as an immunogen to raise enzyme-specific antibodies. Such antibodies are useful as both research reagents (such as in the study of VLCFA regulation in plants) as well as diagnostically to determine expression levels of the enzyme in agricultural products, including pollen.

By way of example only, high level expression of the CUT1 protein may be achieved by cloning and expressing the cDNA in yeast cells using the pYES2 yeast expression vector (Invitrogen, San Diego, Calif.). Secretion of the recombinant CUT1 from the yeast cells may be achieved by placing a yeast signal sequence adjacent to the CUT1 coding region. A number of yeast signal sequences have been characterized, including the signal sequence for yeast invertase. This sequence has been successfully used to direct the secretion of heterologous proteins from yeast cells, including such proteins as human interferon (Chang et al., 1986), human lactoferrin (Liang and Richardson, 1993) and prochymosin (Smith et al., 1985). Alternatively, the enzyme may be expressed at high level in standard prokaryotic expression systems, such as E. coli.

XI. Assays for VLCFA Elongase Activity

To aid the biochemical characterization of the CUT1 protein, or variants of this protein, the very long chain fatty acid elongase activity of the proteins may be determined by expressing the cDNA molecule which encodes protein in question in yeast. For that purpose, the full-length coding region of the cDNA may be linked to the galactose inducible GALL promoter in the *Saccharomyces cerevisiae* expression vector, pYES2 (Invitrogen). The yeast expressing the subject protein may then be employed to determine the substrate specificity of the CUT1 protein by one of the following approaches.

a. In Vitro Assay for VLCFA Elongase Activity Using Cell-free Yeast Homogenate

To determine the range of substrates recognized by the subject protein, acyl elongation activity is measured using substrates of varying carbon chain lengths and degrees of unsaturation. In each case, 15 $\mu$M of an[1-$^{14}$C]acyl CoA (C18, C20, C22, C24 in 0.005% Triton X-100) is added to a standard assay mixture containing 80 mM Hepes-KOH, pH 7.2, 5% glycerol, 1 mM DTT, 0.5 mM NADPH, 1 mM ATP, 5 mM $MgCl_2$, 1 mM malonyl-CoA, and an aliquot of cell free extract (50 $\mu$g protein) in a final volume of 50 $\mu$L. Incubation is carried out at 30° C. for 1 h. The reaction is stopped with 100 $\mu$L of 4 N KOH in 80% methanol and the lipids saponified for 1 h at 80° C. The mixture is then acidified by adding 100 $\mu$L of cold 6N HCL and extracted twice with 500 $\mu$L of cold hexane. The pooled hexane fractions are dried under $N_2$, followed by transmethylation for product analyses.

b. In Vivo Assay: Feeding of Transformed Yeast Cells with Radiolabelled Acyl-tween Substrates A second approach for determining substrate specificity involves growth of yeast cells in the presence of various [1-$C^{14}$]acyl-Tween substrates (C18, C20, C22, C24; Terzaghi, 1986). Fatty acyl substrates provided in the growth medium as Tween-fatty acid esters are readily taken up from the medium and used by the cells. For each FAE protein, yeast cells are initially grown in the presence of several concentrations of a single acyl-Tween substrate for different lengths of time to determine the optimal substrate concentration and the duration of the feeding assays. Once these parameters are established, yeast cells expressing the subject protein and control cells containing empty pYES2 plasmid are grown in a defined medium in the presence of a single radiolabelled acyl-Tween substrate. At the end of the experiment, cells are pelleted, and then resuspended in 1 mL of 1 N methanolic-HCl (Supelco). Treatment with methanolic-HCl converts fatty acids to methyl esters (FAME). Radiolabelled FAMEs are analyzed as described bellow, to characterize the products generated by elongation of each acyl-Tween substrate. A comparison of radiolabelled FAMEs from CUT1 containing yeast with FAMEs isolated from control cells allows the determination of the elongation specificity of the subject FAE protein.

c. Product Analyses

The products of the elongation assays obtained in (a), or pelleted yeast cells from experiment (b) are transmethylated in a sealed tube using 1 N methanolic-HCl (Supelco) at 80° C. for 1 h. Samples are then extracted twice with 500 $\mu$L of hexane after the addition of 1 mL of 0.9% NaCl, and the pooled extracts containing FAMEs concentrated under $N_2$. Radiolabelled FAMEs are applied on $KC_{18}$ reverse-phase TLC plates (Whatman), and separated in acetonitrile:tetrahydrofuran (85:15, v/v). Products of TLC separation are identified by co-chromatography with FAME standards, or by GC-MS. In addition, FAMEs may be scraped from the TLC plates and their radioactivity determined by liquid scintillation counting.

EXAMPLES

The following examples serve to illustrate various applications of the present invention.

Example One

Modification of *A. thaliana* Wax Production By Transformation with the CUT1 cDNA a. Construction of Binary Transformation Vector The CUT1 cDNA was cleaved out of the vector λZipLox (with Kpn1-BamH1) and the resulting 1.85 kb fragment was directionally subcloned into the Kpn1-BamH1 sites of pGEM7z(f) (Promega, Madison, Wis.). The resulting plasmid was then fully cleaved with Xho1, but only partially cleaved with Sst1, (since the CUT1 cDNA has an internal Sst1 site). The 1.9 kb product was isolated on an agarose gel and directionally subcloned into the Sal1 and Sst1 sites of the vector pJD330 (Shaul and Galili 1992). This vector contains the 35S promoter of the cauliflower mosaic virus (CaMV) which provides constitutive expression in Arabidopsis. The subcloning results in the CUT1 cDNA being inserted in a sense orientation with respect to the CaMV 35S promoter. The JD330-CUT1 cDNA construct was ligated with pBIN19 and the resulting binary vector was designated p35S-CUT1. This binary vector was transformed into the *Agrobacterium tumefaciens* strain GV3101 (Koncz and Schell, 1986), and transformants were selected on LB medium containing 25 μg/mL gentamycin and 50 μg/mL kanamycin.

b. Transformation of Arabidopsis with the p35S-CUT1 Transgene

*Arabidopsis thaliana* (L.) Heynh. ecotype Columbia was transformed using a combination of in planta (Chang et al., 1994, Katavic et al., 1994) and vacuum infiltration methods (Bechtold et al., 1993). Plants were grown until the primary inflorescence shoots reached 1–2 cm in height, and then these bolts were cut off. The wound site was inoculated with 50 mL of an overnight Agrobacterium culture harbouring the p35S-CUT1 plasmid. After 4–6 days a number of secondary inflorescences that appeared were cut off, and vacuum infiltration was performed on these plants using the conditions described by Bechtold et al. (1993). Screening for transformed seed was done as described previously (Katavic et al., 1994). Briefly, seed from infiltrated plants were plated out (approximately 1500 seeds/plate) on solid minimal salts nutrient medium supplemented with 50 μg/mL kanamycin. Seedlings that showed resistance were visible after approximately 8 days, because they turned green and elongated. Plants that were derived from seed harvested from different pots were considered as independent lines. Designations of transformed plants were as follows: the infiltrated plant—T1; primary transformants—T2; etc., as outlined in Katavic et al. (1994). Plants were grown at 20° C. under continuous fluorescent illumination (100 $\mu Em^{-2}/s$).

c. CUT1-suppressed Plants Have Altered Wax Composition

Using the above transformation methods 46 kanamycin-resistant plants were obtained from seven different pots of Arabidopsis. Of the 46 plants obtained, 36 appeared waxless, having a glossy or eceriferum (cer) phenotype. At least one cer line was obtained from each pot implying that at least seven independent events had occurred in obtaining these lines. The surfaces of these cer plants were examined by a scanning electron (SE) microscope. SE micrographs clearly demonstrate that while wild-type plants were covered with the characteristic crystals of the epicuticular wax layer, transgenic cer plants were completely devoid of any wax crystals, implying that a severe cer phenotype has been created.

Plant tissue from the transgenic lines was analyzed for fatty acid composition. Plant tissue was immersed for 10 seconds in a 2:1 chloroform:methanol solution to remove surface waxes. Extracts were then evaporated to dryness under a stream of nitrogen. Waxes were dissolved in 100 μl of N,O-bis(Trimethylsilyl)trifluoroacetamide with 1% Trimethylchlorosilane (Pierce), and derivatized at 80° C. for 1 hour. Samples were analyzed in a Hewlett-Packard 5890 series II gas chromatograph equipped with a flame ionization detector, using either a DB-1 column or a DB-5 column.

GLC analyses were performed at the initial temperature of 150° C., followed by a ramping of 4° C./min to 320° C., where it was held for 10 min. Peaks were identified by the comparison of retention times to reference standards, and mass spectrometry. Quantification was based on flame ionization detector peak areas, which were converted to mass units by comparison to the internal standard, 17:0-methylester, which was added to each sample prior to the extraction.

For wax load determinations only the principal surface lipids were measured, n-nonacosane (C29 alkane), 14- and 15-nonacosanol (C29 secondary alcohol), 15-nonacosanone (C29 ketone), C22–C30 aldehydes, C22–C30 primary alcohols and C16–C30 fatty acids (Hannoufa et al., 1993). The total area % of these peaks accounted for more than 90% of the total area % of the sample.

The wax constituents that are found on the stems of Arabidopsis plants originate from two biosynthetic pathways (FIG. 1). The decarbonylation pathway is the major pathway, which utilizes aldehydes to produce alkanes, secondary alcohols and ketones. In Arabidopsis (ecotype Columbia), the C29 species of the wax components produced by this pathway account for almost 90% of all the stem wax. The second pathway, the acyl-reduction pathway, produces primary alcohols, which account for approximately 5% of the total stem wax. Fatty acids and aldehydes, which are precursors for all the other wax components, are shared by both biosynthetic pathways and make up the remaining 5%.

Wax composition and quantity on the stems of wild-type and several transgenic lines were examined. Wild-type Arabidopsis stems contained on average 7106 (+/−) 1184 mg of wax/g dry wt. In contrast, wax loads on the stems of all shiny CUT1-suppressed lines were severely reduced. For example, the wax load on the stems on the most severe line #5 totals 483 (+/−) 83, only 6–7% of the wild-type wax accumulation.

Analysis of wax composition of CUT1-suppressed plants revealed that the decarbonylation pathway is almost completely shut down. The C30 aldehyde, C29 alkane, C29 secondary alcohol and C29 ketone reach only 3.5 %, 2.2%, 1.4% and 2.2% of the levels found on wild-type plants, respectively. CUT1-suppression also has a major effect on the acyl-reduction pathway, causing a reduction in the levels of primary alcohols of over 50%. In addition, the relative abundance of different classes of alcohols is changed. C30 and C28 alcohols, the major alcohol species in wild type stems, have decreased by 90%, and C24 alcohol is the most abundant class in CUT1 suppressed lines. The C24 species are also the most abundant classes of aldehydes and fatty acids in waxless transgenic plants. The described compositional changes were consistent in all 13 different CUT1- suppressed lines analyzed. These changes support the proposal that the role of the CUT1 enzyme is elongation of the fatty acyl chain beyond 24 carbons.

Example Two

Production of Conditionally Male Sterile CUT1-suppressed Plants

CUT1-suppressed Arabidopsis plants were produced as described in Example one and analyzed for male sterility. This analysis demonstrated that, in addition to stem and leaf wax synthesis, the CUT1 gene product has an essential role in pollen development. Similar to cer6-2 (Preuss et al., 1993) and cer1 (Aarts et al., 1995) wax-deficient mutants of Arabidopsis, CUT1-suppressed plants are completely male sterile under normal growth conditions (30 to 40% relative humidity) although they produce normal amounts of pollen. However, when grown under high humidity (90 to 100%), pollen fertility is restored to the wild-type level, indicating that male sterility/fertility is conditional and environmentally controlled, just like in cer6-2 and cer1 mutants. For these two mutants, conditional male sterility is explained by alterations in the composition and content of the wax components of the tryphine layer covering the pollen grain. These long chain lipid molecules, produced in the tapetum layer of the anther, (Preuss et al., 1993) are needed in the tryphine for proper pollen-pistil signalling and pollen germination. Thus, in their absence, sterility occurs. Conditional male sterility is a valuable trait for plant breeders; being able to selectively inhibit self-fertilization of plants facilitates the production of hybrid plants. Accordingly, the CUT1 cDNA and derivatives thereof may be useful in producing conditionally male sterile plants useful in breeding programs.

Taken together, the results of Examples one and two confirm that CUT1 encodes a condensing enzyme that is involved in VLCFA biosynthesis of waxes which accumulate in the plant epidermis, as well as waxes required for the development of functional pollen grains. In addition the results show that transformation of plants using the CUT1 cDNA is useful to produce plants having modified VLCFA compositions, as well as plants that exhibit conditional male sterility.

Example Three

Use of CUT1 Gene Promoter Sequence

The promoter of the CUT1 gene confers epidermis-specific expression. Accordingly, this promoter sequence may be used to produce transgene constructs that are specifically expressed in epidermal cells. Effective epidermis-specific expression may be achieved with less than the entire 1951 bases of sequence upstream of the CUT1 ORF shown in Seq. I.D. No. 12. Thus, by way of example, epidermis-specific expression may be obtained by employing the 1209 base pair promoter fragment. One of skill in the art will recognize that still smaller regions of the sequence upstream of the CUT1 ORF may be used to obtain epidermis-specific expression, such as a 50 base pair or 100 base pair region of the disclosed promoter sequence.

The determination of whether a particular sub-region of the disclosed sequence operates to confer effective epidermis-specific expression in a particular system (taking into account the plant species into which the construct is being introduced, the level of expression required, etc.) will be performed using known methods, such as operably linking the promoter sub-region to a marker gene (e.g. GUS), introducing such constructs into plants and then determining the level of expression of the marker gene in epidermis and other plant tissues.

The present invention therefore facilitates the production, by standard molecular biology techniques, of nucleic acid molecules comprising this promoter sequence operably linked to a nucleic acid sequence, such as an open reading frame. Suitable open reading frames include open reading frames encoding any protein for which epidermis-specific expression is desired.

Having illustrated and described the principles of isolating CUT1 nucleic acids, the CUT1 protein and modes of use of these biological molecules, it should be apparent to one skilled in the art that the invention can be modified in arrangement and detail without departing from such principles. We claim all modifications coming within the spirit and scope of the claims presented herein.

References

Aarts et al., (1997). The Arabidopsis MALE STERILITY 2 protein shares similarity with reductases in elongation/condensation complexes. *Plant J*.12:615–623.

Aarts et al., (1995). Molecular characterization of the CER1 gene of Arabidopsis involved in epicuticular wax biosynthesis and pollen fertility. *Plant Cell* 7:2115–2127.

Altschul et al., (1994). *Nature Genet.*, 6:119–129.

An et al., (1988). *Plant Physiol.* 88:547.

Ausubel et al., (1987). In *Current Protocols in Molecular Biology*, Greene Publishing Associates and Wiley-Intersciences.

Battey et al., (1989). "Genetic Engineering for Plant Oils: Potential and Limitations." *TIBTECH* 7:122–125.

Bechtold and Pelletier, (1993). "*In planta Agrobacterium* Mediated Gene Transfer by Infiltration of Adult *Arabidopsis thaliana* Plants." *C.R. Acad. Sci. Paris* 316:1194–1199.

Bolton and McCarthy, (1962). *Proc. Natl. Acad. Sci. USA* 48:1390.

Bonner et al., (1973). *J. Mol. Biol.* 81:123.

Bustos et al., (1989). *Plant Cell* 1:839.

Callis et al., (1988). *Plant Physiol.* 88:965.

Carpenter et al. (1992). Preferential expression of an -tubulin gene of Arabidopsis in pollen. *The Plant Cell* 4:557–571.

Chang et al., (1994). "Stable Genetic Transformation of *Arabidopsis thaliana* by Agrobacterium inoculation in planta." *Plant J.* 5: 551–558.

Chang et al., (1994). Stable genetic transformation of *Arabidopsis thaliana* by Agrobacterium inoculation in planta. *Plant J.* 5:551–558.

Chang et al. (1986) *Saccharomyces cerevisiae* secretes and correctly processes human interferon hybrid protein containing yeast invertase signal peptides. *Mol. And Cell. Biol.* 6:1812–1819.

Cheesbrough and Kolattukudy, (1984). *Proc. Natl. Acad. Sci.* 81:6613–6617.

Corpet et al. (1988). *Nucleic Acids Research* 16:10881–90.

Dekeyser et al., (1990). *Plant Cell* 2:591.

Denis et al. (1993). Expression of engineered nuclear male sterility in *Brassica napus*. *Plant Physiol.* 101:1295–1304.

Dooner, (1990). *Theor. Appl. Genet.* 80: 241–245.

Eigenbrode and Espelie, (1995). Effects of plant epicuticular lipids on insect herbivores. *Annu. Rev. Entomol.* 40:117–142.

Fehling and Mukherjee, (1991). "Acyl-CoA Elongase From a Higher Plant (*Lunaria annua*): Metabolic Intermediates of Very-long-chain Acyl-CoA Products and Substrate Specificity." *Biochem. Biophys. Acta* 1082: 239–246.

Fischer et al., (1997). Stilbene synthase gene expression causes changes in flower colour and male sterility in tobacco. *Plant J.* 11:489–498.

Fromm et al., (1989). *Plant Cell* 1:977.

Gan & Amansino, (1995). Inhibition of leaf senescence by autoregulated production of cytokinin. *Science* 270:1986–1988.

Gelvin et al., (1990). Plant Molecular Biology Manual, Kluwer Academic Publishers.

Goldberg et al., (1993). Anther development: Basic principles and practical applications. *Plant Cell* 5:1217–1229.

Hannoufa et al., (1993). Epicuticular waxes of Eceriferum mutants of *Arabidopsis thaliana*. *Phytochemistry* 33: 851–855.

Haque et al., (1992). Inheritance of leaf epicuticular wax content in rice. *Crop Sci.* 32:865–868.

Higgins & Sharp, (1988). *Gene,* 73:237–244.

Innis et al. (1990). *PCR Protocols, A Guide to Methods and Applications,* Innis et al. (eds.), Academic Press, Inc., San Diego, Calif.

James et al. (1995). "Directed Tagging of the Arabidopsis FATTY ACID ELONGATION (FAE1) Gene With the Maize Transposon Activator." *Plant Cell* 7:309–319.

James and Dooner, (1990). "Isolation of EMS-induced Mutants in Arabidopsis Altered in Seed Fatty Acid Composition." *Theor. Appl. Genet.* 80:241–245.

Jefferson et al., (1987). GUS fusions: β-glucuronidase as a sensitive and versatile gene fusion marker system in higher plants. *EMBO J.* 6:3901–3907.

Jenks et al., (1994). *Plant Physiol.* 105:1239–1245.

Johnson and Fritz, (1989). "Fatty Acids in Industry." New York:Marcel Dekker.

Katavic et al. (1994). "In planta Transformation of *Arabidopsis thaliana."* *Mol. Gen. Genet.* 245: 363–370.

Kolattukudy, (1971). *Arch. Biochem. Biophys.* 142:701–709.

Koncz and Schell, (1986). The promoter of $T_L$-DNA gene 5 controls the tissue-specific expression of chimaeric genes carried by a novel type of Agrobacterium binary vector. *Mol. Gen. Genet.* 204:383–396.

Kuhlemeier et al., (1989). *Plant Cell* 1:471.

Kunst et al., (1992). "Fatty Acid Elongation in Developing Seeds of *Arabidopsis thaliana."* *Plant Physiol. Biochem.* 30:425–434.

Lassner et al., (1996). "A Jojoba β-ketoacyl-CoA Synthase cDNA Complements the Canola Fatty Acid Elongation Mutation in Transgenic Plants." *Plant Cell* 8: 281–292.

Lee and Douglas (1996). Manipulation of plant gene expression using antisense RNA. In: *Plant Biochemistry/Molecular Biology Laboratory Manual,* pp. 423–439, Dashek, W. V., ed., CRC Press, Inc., Boca Raton.

Lee et al., (1991). *Proc. Natl. Acad. Sci. USA* 88:6181–6185.

Lemieux et al., (1990). "Mutants of Arabidopsis With Alterations in Seed Lipid Fatty Acid Composition." *Theor. Appl. Genet.* 80:234–240.

Lemieux, (1996). *Trends in Plant Sci.* 1:312–318.

Liang & Richardson, (1993). Expression and characterization of human lactoferrin in yeast (*Saccharomyces cerevisiae*). *J. Agric. Food Chem.* 41:1800–1807.

Marcotte et al., (1989). *Plant Cell* 1:969.

Mariani et al., (1990). Induction of male sterility in plants by a chimaeric ribonuclease gene. *Nature* 347:737–741.

Millar and Kunst, (1997). Very-long-chain fatty acid biosynthesis is controlled through the expression and specificity of the condensing enzyme. *Plant J.* 12:121–131.

Nacken et al., (1991). Molecular characterization of two stamen-specific genes, tap1 and fil1, that are expressed wild type, but not the deficiens mutant of *Anthirrhinum majus. Mol. Gen. Genet.* 229:129–136.

Needleman & Wunsch, (1970). *J. Mol. Biol.* 48:443.

O'Toole and Cruz, (1983). Genotypic variation in epicuticular wax of rice. *Crop Sci.* 23:392–394.

Odel et al., (1985). *Nature* 313:810.

Odell et al., (1994). Seed specific gene activation mediated by the Cre/lox site-specific recombination system. *Plant Physiol.* 106:447–458.

Opperman et al., (1993). Root knot nematode directed expression of a plant root specific gene. *Science* 263:221–223.

Pearson & Lipman, (1988). *Proc. Natl. Acad. Sci. USA* 85:2444.

Pearson et al., (1994). *Methods in Molecular Biology* 24:307–31.

Percy and Baker, (1990). *New Phytol.* 116:79–87.

Post-Beittenmiller, (1996). "Biochemistry and Molecular Biology of Wax Production in Plants." *Annu. Rev. Plant Physiol. Mol. Biol.* 47: 405–430.

Pouwels et al., (1987). Cloning Vectors: A Laboratory Manual, 1985, supp.

Preuss et al., (1993). A conditional sterile mutation eliminates surface components from Arabidopsis pollen and disrupts cell signalling during fertilization. *Genes & Development* 7:974–985.

Reicosky and Hanover, (1978). "Physiological Effects of Surface Waxes. 1. Light Reflectance for Glaucous and Nonglaucous Picea Pungens". *Plant Physiol.* 62:101–104.

Roshal et al., (1987). *EMBO J.* 6:1155.

Sambrook et al., (1989). *In Molecular Cloning: A Laboratory Manual,* Cold Spring Harbor, N.Y.

Schaffner and Sheen, (1991). *Plant Cell* 3:997.

Schernthaner et al., (1988). *EMBO J.* 7:1249.

Schreiber and Schonherr, (1992). *Pesti. Sci.* 36:213–221.

Siebertz et al., (1989). *Plant Cell* 1:961.

Smith & Waterman, (1981). *Adv. Appl. Math.* 2:482.

Smith et al., (1985). Heterologous protein secretion from yeast. *Science* 229:1219–1224.

Southern, (1975). *J. Mol. Biol.* 98:503.

Simpson et al., (1985). *EMBO J.* 4:2723.

Stefansson et al., (1961). "Note on the Isolation of Rape Plants With Seed Oil Free From Erucic Acid." *Can. J. Plant Sci.* 41:218–219.

Stockhause et al., (1997). The promoter of the gene encoding the $C_4$ form of phosphoenolpyruvate carboxylase directs mesophyll-specific expression in transgenic $C_4$ Flaveria spp. The Plant Cell 9:479–489.

Terada and Shimamoto, (1990). *Mol. Gen. Genet.* 220:389.

Tijssen, (1993). *Laboratory Techniques in Biochemistry and Molecular Biology—Hybridization with Nucleic Acid Probes* Part I, Chapter 2 "Overview of principles of hybridization and the strategy of nucleic acid probe assays", Elsevier, N.Y.

Tsuchiya et al., (1995). Tapetum-specific expression of the gene for an endo-betabeta-1,3-glucanase causes male-sterility in transgenic tobacco. *Plant Cell Physiol.* 36:487–494.

van der Krol et al., (1988). An antisense chalcone synthase gene in transgenic plants inhibits flower pigmentation. *Nature* 333:866–869.

van der Krol et al., (1990). Inhibition of Plower pigmentation by antisense chs genes: promoter and minimal sequence requirements for the antisense effect. *Plant Mpl. Biol.* 14:457–466.

van der Meer et al., (1992). Antisense inhibition of flavonoid biosynthesis in petunia anthers results in male sterility. *Plant Cell* 253:–262.

Voelker et al., (1992). Fatty acid biosynthesis redirected to medium chains in transgenic oilseed plants. *Science* 257:72–74.

von Wettstein-Knowles, (1982). "Elongase and Epicuticular Wax Biosynthesis." *Physiol. Veg.* 20:797–809.

Weissbach and Weissbach, (1989). Methods for Plant Molecular Biology, Academic Press.

Worrall et al., (1992). Premature dissolution of the microsporocyte callose wall causes male sterility in transgenic tobacco. *Plant Cell* 4:759–771.

We claim:

1. A recombinant nucleic acid molecule comprising a promoter sequence operably linked to a nucleic acid sequence, wherein the promoter sequence comprises a transcriptional regulatory region capable of mediating gene expression in epidermal cells of Arabidopsis wherein the transcriptional regulatory region hybridezes under stringent conditions to: Seq. I.D. No. 12 or the complement of Seq. I.D. No. 12.

2. A recombinant nucleic acid molecule according to claim 1 wherein the promoter sequence comprises at least 50 consecutive nucleotides of the sequence shown in Seq. I.D. No. 12 or the complement of Seq. I.D. No. 12.

3. The recombinant nucleic acid molecule according to claim 1, wherein the promoter sequence is at least 70% identical to the sequence set forth in Seq. I.D. No. 12.

4. A recombinant nucleic acid molecule according to claim 1, wherein the promoter sequence is at least 80% identical with the sequence set forth in Seq. I.D. No. 12 or the complement of Seq. I.D. No. 12.

5. A recombinant vector comprising a nucleic acid molecule according to claim 1.

6. A transgenic plant comprising a heterologous nucleic acid sequence, wherein the heterologous nucleic acid sequence comprises the recombinant nucleic acid molecule of claim 1.

7. The recombinant nucleic acid molecule according to claim 1, wherein the nucleic acid sequence encodes a protein having very long chain fatty acid elongase activity.

8. A method of producing a transgenic plant comprising introducing into the plant the recombinant nucleic acid molecule of claim 1.

9. A plant produced by sexual or asexual propagation of the transgenic plant produced according to the method of claim 8, or by propagation of progeny of the transgenic plant, wherein the plant comprises the recombinant nucleic acid molecule.

10. A method of isolating a nucleic acid molecule having promoter activity, comprising hybridizing under stringent conditions a nucleic acid preparation with a probe comprising Seq. I.D. No. 12 or the complement of Seq. I.D. No. 12.

11. A plant cell comprising a heterologous nucleic acid sequence, wherein the heterologous nucleic acid sequence comprises the recombinant nucleic acid molecule of claim 1.

12. A recombinant nucleic acid molecule comprising a promoter sequence operably linked to a nucleic acid sequence, wherein the promoter sequence comprises a transcriptional regulatory region capable of mediating gene expression in epidermal cells of Arabidopsis wherein the transcriptional regulatory region is obtainable from a plant VLCFA condensing enzyme gene comprising an open reading frame that hybridizes under stringent conditions to Seq. I.D. No. 3 or to the complement of Seq. I.D. No. 3.

* * * * *